United States Patent
Geromanos et al.

(10) Patent No.: US 10,825,672 B2
(45) Date of Patent: Nov. 3, 2020

(54) TECHNIQUES FOR MASS ANALYZING A COMPLEX SAMPLE BASED ON NOMINAL MASS AND MASS DEFECT INFORMATION

(71) Applicant: WATERS TECHNOLOGIES CORPORATION, Milford, MA (US)

(72) Inventors: Scott J. Geromanos, Middletown, NJ (US); Curt Devlin, Fairhaven, MA (US); Steven J. Ciavarini, Natick, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 15/819,793

(22) Filed: Nov. 21, 2017

(65) Prior Publication Data

US 2018/0144918 A1    May 24, 2018

Related U.S. Application Data

(60) Provisional application No. 62/424,699, filed on Nov. 21, 2016.

(51) Int. Cl.
  *H01J 49/00* (2006.01)
  *G16B 40/00* (2019.01)
  *G16B 20/00* (2019.01)

(52) U.S. Cl.
  CPC .......... *H01J 49/0045* (2013.01); *G16B 20/00* (2019.02); *G16B 40/00* (2019.02); *H01J 49/0036* (2013.01)

(58) Field of Classification Search
  None
  See application file for complete search history.

(56) References Cited

U.S. PATENT DOCUMENTS

| | | | |
|---|---|---|---|
| 2007/0038387 A1* | 2/2007 | Chen | H01J 49/0036 702/23 |
| 2013/0282293 A1 | 10/2013 | Geromanos et al. | |
| 2016/0003842 A1 | 1/2016 | Lee et al. | |

OTHER PUBLICATIONS

Williams et al., Multi-mode acquisition (MMA): An MS/MS acquisition strategy for maximizing selectivity, specificity and sensitivity of DIA product ion spectra. Proteomics, 16: 2284-2301 (2016) (Year: 2016).*

(Continued)

*Primary Examiner* — James Choi

(57) ABSTRACT

Techniques and apparatus for analyzing mass spectrometry data are described. In one embodiment, for example, an apparatus may include logic to access a product ion data set generated via mass analyzing a sample comprising a target precursor, access precursor composition information for elements of the target precursor that includes nominal mass and mass defect information, determine nominal mass (NM)-mass defect (MD) relationship information for ion fragments associated with the target precursor based on the precursor composition information, determine one or more fragment upper boundaries and one or more fragment lower boundaries, extract candidate ion fragments from the ion fragments via applying the one or more fragment upper boundaries and the one or more fragment lower boundaries to the NM-MD relationship information, and determine target ion fragments from the plurality of candidate ion fragments based on fragmentation efficiency information associated with the candidate ion fragments. Other embodiments are described and claimed.

22 Claims, 17 Drawing Sheets

(56) References Cited

OTHER PUBLICATIONS

Toumi et al., Improving Mass Defect Filters for Human Proteins, J. Proteome Res. 2010, 5492-5495 (Year: 2010).*

Williams et al., Multi-mode acquisition (MMA): An MS/MS acquisition strategy for maximizing selectivity, specificity and sensitivity of DIA product ion spectra. Proteomics, 16: 2284-2301 (2016) (supplemental info) (Year: 2016).*

International Search Report and Written Opinion for International Application No. PCT/US2017/062811 dated Feb. 19, 2018.

Williams, B. et al., "Multi-mode acquisition (MMA): An MS/MS acquisition strategy for maximizing selectivity, specificity and sensitivity of DIA product ion spectra," Proteomics, vol. 16, No. 15-16, pp. 2284-230, Aug. 1, 2016.

Toumi, M. et al., "Improving Mass Defect Filters for Human Proteins," Journal of Proteome Research., vol. 9, No. 10, pp. 5492-5495, Oct. 1, 2010.

* cited by examiner

*FIG. 2*

| Table 2 305 ||
|---|---|
| Amino Acid 310 | Distribution 315 |
| A | 0.065584 |
| C | 0.020820 |
| D | 0.053091 |
| E | 0.067666 |
| F | 0.041640 |
| G | 0.062461 |
| H | 0.022902 |
| I | 0.052050 |
| K | 0.065584 |
| L | 0.100568 |
| M | 0.020820 |
| N | 0.052050 |
| P | 0.054132 |
| Q | 0.049968 |
| R | 0.054132 |
| S | 0.83281 |
| T | 0.060389 |
| V | 0.031230 |
| W | 0.010410 |
| Y | 0.031230 |

```
DETERMINE A TARGET PRECURSOR OF A SAMPLE FOR MASS
ANALYSIS
1202
          │
          ▼
ACCESS PRECURSOR COMPOSITION INFORMATION FOR
ELEMENTS OF THE TARGET PRECURSOR
1204
          │
          ▼
DETERMINE NM-MD RELATIONSHIP INFORMATION FOR ION
FRAGMENTS ASSOCIATED WITH THE TARGET PRECURSOR
1206
          │
          ▼
DETERMINE AN ION FRAGMENT UPPER BOUNDARY AND AN
ION FRAGMENT LOWER BOUNDARY FOR THE ION
FRAGMENTS
1208
          │
          ▼
EXTRACT CANDIDATE ION FRAGMENTS BASED ON APPLYING
THE ION FRAGMENT UPPER BOUNDARY AND THE ION
FRAGMENT LOWER BOUNDARY TO THE NM-MD
RELATIONSHIP INFORMATION
1210
```

*FIG. 12*

TECHNIQUES FOR MASS ANALYZING A COMPLEX SAMPLE BASED ON NOMINAL MASS AND MASS DEFECT INFORMATION

CROSS-REFERENCE TO RELATED APPLICATION

This application claims the benefit of priority of 35 U.S.C. § 119(e) to U.S. Provisional Patent Application Ser. No. 62/424,699, filed on Nov. 21, 2016, which is incorporated by reference in its entirety as if fully set forth herein.

TECHNICAL FIELD

Embodiments herein generally relate to analysis of a complex sample and, more particularly, to quantitation of compounds in a complex sample by mass spectrometry (MS).

BACKGROUND

The ability to acquire both accurate and precise qualitative and quantitative mass spectral data in the analysis of complex systems, such as proteins or other complex compounds, is predicated on the ability to measure the physicochemical attributes of all ions independent of any surrounding matrix. Successful qualitative analysis requires ensuring that fragment and product ions are correctly aligned or matched to the parent or precursor ions from which they were derived.

MS coupled with chromatography, such as liquid chromatography (LC) methods, is a common approach to quantifying compounds in a sample. For example, MS/MS (or tandem MS) relates to a product ion spectrum of fragment ion from one or more precursor ions generated by a mechanism of disassociation, such as in-source fragmentation, surface-induced fragmentation, collision-induced dissociation, electron capture, electron-detachment, charge transfer, and photodissociation. The quantitation is typically performed by first separating compounds by LC to generate a sequence of chromatograms, then ionizing and detecting the separated compounds by MS/MS to produce a plurality of mass spectra having ion peaks. Using a peak area or a sum area of all peaks within a mass window that are associated with a target compound, quantitative information may be inferred about the compound of interest, assuming there is a correlation between the peak area and the compound concentration.

Structural elucidation of molecules in complex samples is determining which fragment ions in a product ion spectrum belong to which precursor. Conventional approaches experience challenges in quantifying a target compound in a complex sample, particularly under the time and resource constraints expected by operators and researchers. For example, as the complexity or dynamic range of a sample increases, the chance of multiple compounds co-eluting from LC in a same retention time (RT) window is also magnified, resulting in mass spectra where ions from different compounds occupy a same mass-to-charge-ratio (m/z) space and interfere with each other. In another example, as the complexity of a sample increases, the number of high-abundance compounds in the sample proportionally increases as well, which can saturate a detector and corrupt linearity of detector response. Accordingly, conventional MS techniques are frequently not able to provide a signal profile that is adequately correlated with the quantity of the compounds that constitute complex samples.

SUMMARY

The following presents a simplified summary in order to provide a basic understanding of some novel embodiments described herein. This summary is not an extensive overview, and it is not intended to identify key/critical elements or to delineate the scope thereof. Some concepts are presented in a simplified form as a prelude to the more detailed description that is presented later.

Various embodiments are generally directed to MS techniques for analyzing a sample. For example, some embodiments may include techniques and apparatus operative to segregate product ions in a composite product ion spectrum to their parent precursor ions based on, among other things, mass information of the constituent elements of the molecules under analysis. In exemplary embodiments, product ions may be aligned to their parent precursor via comparison of the rate of change of nominal (or integer) mass and mass defect (or fractional mass), for example, in descending order of nominal mass relative to that of the possible parent precursors.

In an embodiment, a method of sample analysis may include accessing at least one product ion data set generated via mass analyzing a sample comprising at least one target precursor, accessing precursor composition information for a plurality of constituent elements of the at least one target precursor, the precursor composition information comprising nominal mass information and mass defect information for at least a portion of the plurality of constituent elements, determining nominal mass (NM)-mass defect (MD) relationship information for a plurality of ion fragments associated with the at least one target precursor based on the precursor composition information, determining at least one ion fragment upper boundary and at least one ion fragment lower boundary for the plurality of ion fragments, extracting a plurality of candidate ion fragments from the plurality of ion fragments via applying the at least one ion fragment upper boundary and the at least one ion fragment lower boundary to the NM-MD relationship information, determining a plurality of target ion fragments from the plurality of candidate ion fragments based on fragmentation efficiency information associated with the plurality of candidate ion fragments, and generating spectral data for at least a portion of the plurality of target ion fragments of the at least one product ion data set. Other embodiments are described and claimed.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings

BRIEF DESCRIPTION OF THE DRAWINGS

FIG. 2 depicts mass information for constituent elements of a peptide precursor molecule.

FIG. 3 depicts peptide constituent element distribution information.

FIG. 12. illustrates an embodiment of a first logic flow.

DETAILED DESCRIPTION

Various embodiments may be generally directed to methods and apparatus for generating MS spectral data and aligning product ions to precursor molecules. Techniques and embodiments will now be described with reference to illustrative embodiments for analyzing samples, for instance, in a system analyzing samples using an MS process, such as LC/MS/MS. It will be appreciated that the techniques described herein may be used in connection with other systems, methods, and/or embodiments and may have a broader application than provided for purposes of illustration in this detailed description.

In this description, numerous specific details, such as component and system configurations, may be set forth in order to provide a more thorough understanding of various embodiments. It will be appreciated, however, by one skilled in the art, that the embodiments may be practiced without such specific details. Additionally, some well-known structures and other features have not been shown in detail, to avoid unnecessarily obscuring the present invention.

In the following description, references to "one embodiment," "an embodiment," "example embodiment," "various embodiments," etc., indicate that the embodiment(s) of the invention so described may include particular features, structures, or characteristics, but more than one embodiment may and not every embodiment necessarily does include the particular features, structures, or characteristics. Further, some embodiments may have some, all, or none of the features described for other embodiments.

Figure 1:
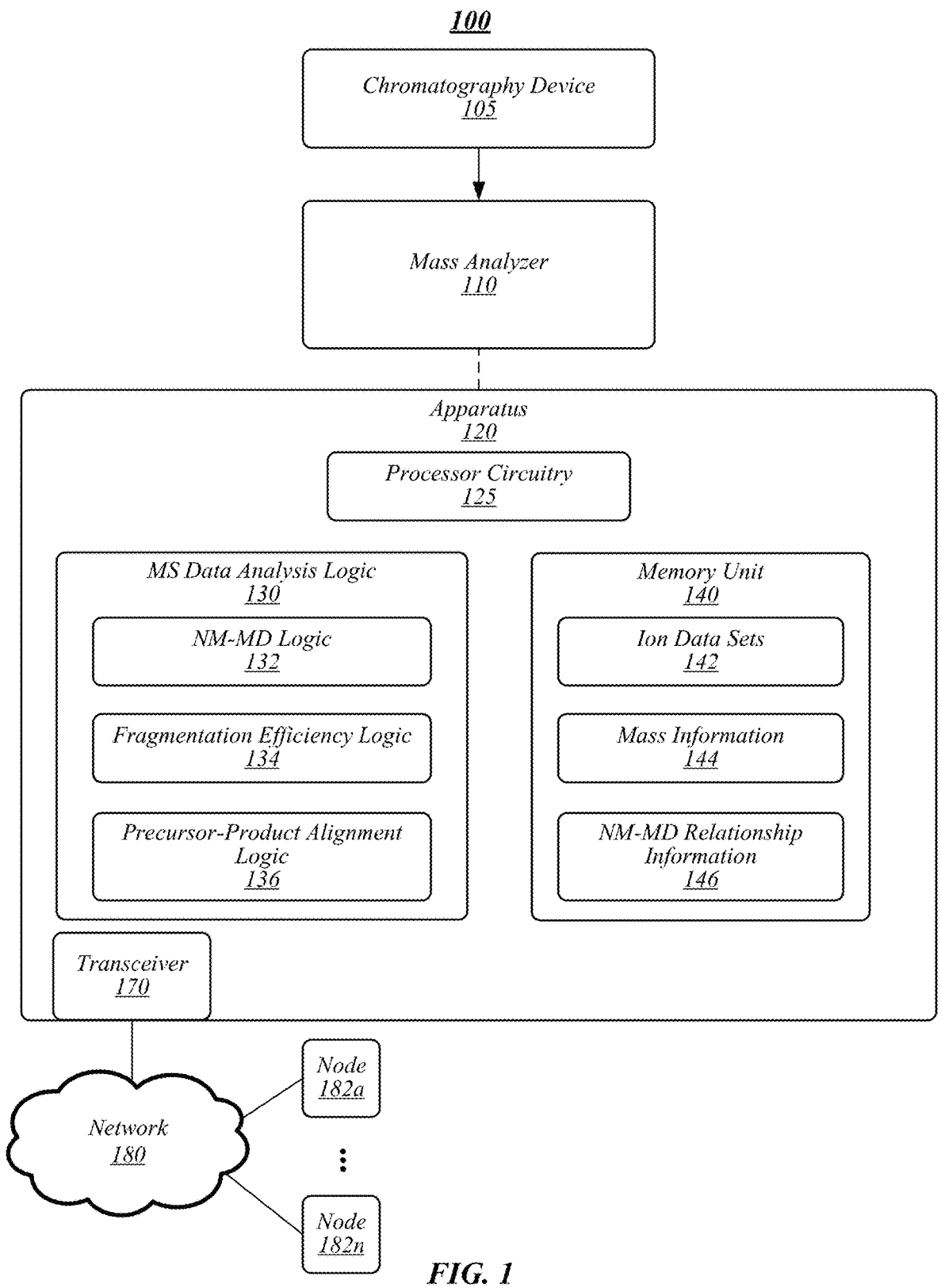
FIG. 1 illustrates an embodiment of a first operating environment.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner FIG. 1 illustrates an example of an operating environment 100 that may be representative of various embodiments. The operating environment 100 depicted in FIG. 1 may include a chromatography device 105, including, without limitation, an LC device. A sample may be injected into chromatography device 105 through an injector. A pump may direct the sample through a column of chromatography device 105 to separate the sample into component parts according to retention time through the column. The output of chromatography device 105 may be directed to a mass spectrometer 110 for analysis. The system of chromatography device 105 and mass spectrometer 110 may be configured, for example, as an LC-MS or LC-MS/MS device. Although LC and MS/MS are used as examples, embodiments are not so limited, as any type of MS system capable of operating according to some embodiments is contemplated herein.

LC-MS and LC-MS/MS acquisition techniques typically involve acquiring one or more parent (precursor) ion data sets (spectra) and one or more corresponding product ion data sets (spectra) for a sample eluting from chromatography device 105. In these techniques, eluent from a liquid chromatography column of chromatography device 105 is passed into an ion source, where it is ionized. A fragmentation, collision or reaction device (or cell) is typically arranged downstream of the ion source to selectively fragment or react parent ions to produce product ions. In MS 110, the output of collision cell is directed to a mass analyzer. The mass analyzer can be any mass analyzer, including, for example, quadrupole, time-of-flight (TOF), ion trap, magnetic sector mass analyzers as well as combinations thereof. A detector of the mass spectrometer detects ions emanating from the mass analyzer. The detector can be integral with mass analyzer. For example, in the case of a TOF mass analyzer, the detector can be a microchannel plate detector that counts intensity of ions, i.e., counts numbers of ions impinging it. For example, MS 110 may include a TOF MS arranged downstream of the fragmentation, collision or reaction device, that may be used used to acquire the parent and product ion data sets After acquiring the data sets, product and parent ions may be detected in the data sets, and product ions are assigned or "binned" to parent ions. Binning may be accomplished, for example, by chromatographic retention time alignment. A product ion may be assigned (binned) to one or more particular parent ions if the product ion's retention time is the same as that of the one or more parent ions, within measurement error. Measurement error is typically taken to be a fraction of the peak width of the one or more parent ions. For example, a product ion may be assigned to one or more particular parent ions if the product ion's retention time is within +/− the half-width at half maximum ("HWHM") of the chromatographic peak width of the one or more parent ions.

Another known acquisition technique additionally makes use of ion mobility. In such arrangements, an ion mobility separation ("IMS") device is arranged downstream of the ion source and upstream of the fragmentation, collision or reaction device. Binning is accomplished by retention time alignment as well as ion mobility alignment. Thus, different components of the sample can more readily be distinguished, and product ions can be more accurately assigned to the appropriate parent ions. However, there are still a significant number of cases where components have retention times and drift times that cannot be distinguished.

MS 110 may be operated according to various acquisition modes of operation. Non-limiting examples of modes of operation may include Data Dependent Acquisition (DDA), Data Independent Acquisition (DIA), and/or variations thereof. In DDA, fragment or product ions are formed from parent or precursor ions that are mass resolved (for example, using a quadrupole mass filter isolation window). In DIA, fragment or product ions are formed from parent or precursor ions that are either time resolved ($MS^E$) or time and ion mobility drift time resolved ($HD-MS^E$).

Precursor and product ion alignment in DDA may include use of the product ions from the isolated (for instance, 1st mass filter precursor) m/z precursor ion being assigned to the parent precursor with no additional filtering other than the width of the m/z isolation window. The assumption is the narrower the mass isolation window the more selective the MS/MS product ion spectra will be. Such a relationship may occur when dealing with simple mixtures; however, a small mass isolation window, even as small as 0.4 Th, may not contain only one precursor molecule when sampling complex mixtures. Biomolecules, for example, primarily constructed of (carbon (C), nitrogen (N), hydrogen (H), oxygen (O), sulfur (S), and phosphorus (P), may create compounds of very different structures albeit nearly identical m/z. Moreover, certain elemental compositions can produce precursor ion m/z values that are nearly identical but of different charge states. Although biomolecules, such as proteins/peptides, are used as examples herein, embodiments are not so limited. Indeed, any type or class of compound capable of being processed and analyzed according to some embodiments is contemplated herein, such as pesticides, hydrocarbons, and/or the like.

Conventional systems generally use one of two commercially available types of DIA, SWATH (Sequential Window Acquisition of all THeoretical Mass Spectra) and MSE. In general, SWATH operates substantially similar to DDA acquisition, however the m/z isolation window width is larger (>10 Thomson (Th)). In MSE, all precursor ions are fragmented all the time within, either, a constant or variable m/z isolation window. Although these types of experiments have higher product ion sampling rates, they are limited in that every MS/MS spectra contains product ions from more than one precursor. SWATH uses spectral libraries for matching product ions between known identifications and the composite product ion spectra. In addition, product ion spectra can also be searched using very wide precursor mass tolerances (for example, the width of the isolation window at all available charge states). For MSE, precursor and product ions are aligned by center mass retention and, if ion mobility separation is applied, centered drift times. Although DIA samples more of the ions complement of a complex sample, the ability to correctly identify and quantify across a wide dynamic range of the added complement of compounds sampled is limited by complexity.

MS 110 may be communicatively coupled to an apparatus 120, such as a computing or logic device, having a processor circuitry 125, a memory unit 140, and a transceiver 170. Processing circuitry 125 may be communicatively coupled to memory unit 140 and/or transceiver 170. In some embodiments, apparatus 120 and/or components thereof may be components of MS 110. In various embodiments, apparatus 120 and/or components thereof may be operative to control MS 110 and/or certain functions thereof.

Processing circuitry 125 may include and/or may access various logic for performing processes according to some embodiments. For instance, processing circuitry 125 may include and/or may access MS data analysis logic 130, for example, NM-MD logic 132, fragmentation efficiency logic 134, and/or precursor-product alignment logic 136. MS data analysis logic 130, for example, NM-MD logic 132, frag-mentation efficiency logic 134, and/or precursor-product alignment logic 136 may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1500 of FIG. 15. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like. In some embodiments, at least a portion of MS data analysis logic 130 (and logic thereof) may be arranged within processor circuitry 125. In other embodiments, for example, MS data analysis logic 130 may be located within an accelerator, a processor core, an interface, an individual processor die, and/or the like.

Transceiver 170 may be operative to provide communication processes for apparatus 120. For example, apparatus 120 may be in communication with nodes 182a-n accessible via network 180 via transceiver 170. Memory unit 140 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 140 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

In some embodiments, various data may be stored in memory unit 140, such as ion data sets 142, mass information 144, and/or nominal mass (NM)-mass defect (MD) relationship information 146. In various embodiments, sample analysis results of MS 110 may be provided to apparatus 120 and stored, for example, as ion data sets 142. Non-limiting examples of ion data sets 142 may include m/z information, retention time information, mobility drift information, intensity information, spectra, and/or the like. In some embodiments, ion data sets 142, mass information 144, and/or NM-MD relationship information 146 may include information accessed and/or stored in one or more remote locations, such as in a database, cloud computing environment, and/or the like.

MS data analysis logic 130 may be operative to provide various analysis processes for data from MS 110. For example, MS data analysis logic 130, alone or via one or more of NM-MD logic 132, fragmentation efficiency logic 134, and/or precursor-product alignment logic 136, may be operative to provide a MS data analysis process to analyze MS data (for instance, ion data sets), generate MS data spectra, align product ions and precursors, and/or the like.

NM-MD logic 132 may be operative to provide various processes relating to mass information associated with one or more molecules being analyzed by MS 110. In some embodiments, one or more molecules may be selected or otherwise designated as a target precursor. In general, a target precursor is the precursor of interest in a MS analysis, such as a particular protein or peptide that is of interest in a complex sample.

NM-MD logic 132 may access, generate, and/or provide mass information 144 associated with the target precursor and/or constituent elements or potential fragments thereof. In various embodiments, mass information 144 may include, but is not limited to, nominal mass and mass defect information of constituent elements (or building blocks) and/or potential fragments of the target precursor. For example, if the target precursor is a peptide, the constituent elements would include amino acids as well as any other potential elements, moieties, and/or the like that may be included in the target precursor. In general, the nominal mass of an element includes the integer mass of the most abundant naturally occurring stable isotope of an element or the sum of the integer masses of the constituent elements of a molecular ion or molecule. The mass defect is the difference between the actual mass of a specific nucleus and the nominal mass. The mass defect may represent the equivalent of the different binding energies required for nuclear stabilization of the different elements. By convention, the mass excess of 12C is defined as zero. The mass defect of the elements may be positive (for example, $^1$H: 1.00783 and $^{14}$N: 14.00307) or negative (e.g. $^{16}$O: 15.99491, $^{32}$S: 31.97207, and $^{31}$P: 30.97376). The mass defect of a compound may include the fractional mass, which is the mass to the right of the decimal point. For example, the amino acid alanine has a nominal mass of 71.03711 and a mass defect or fractional mass of 0.03711.

Figure 2:
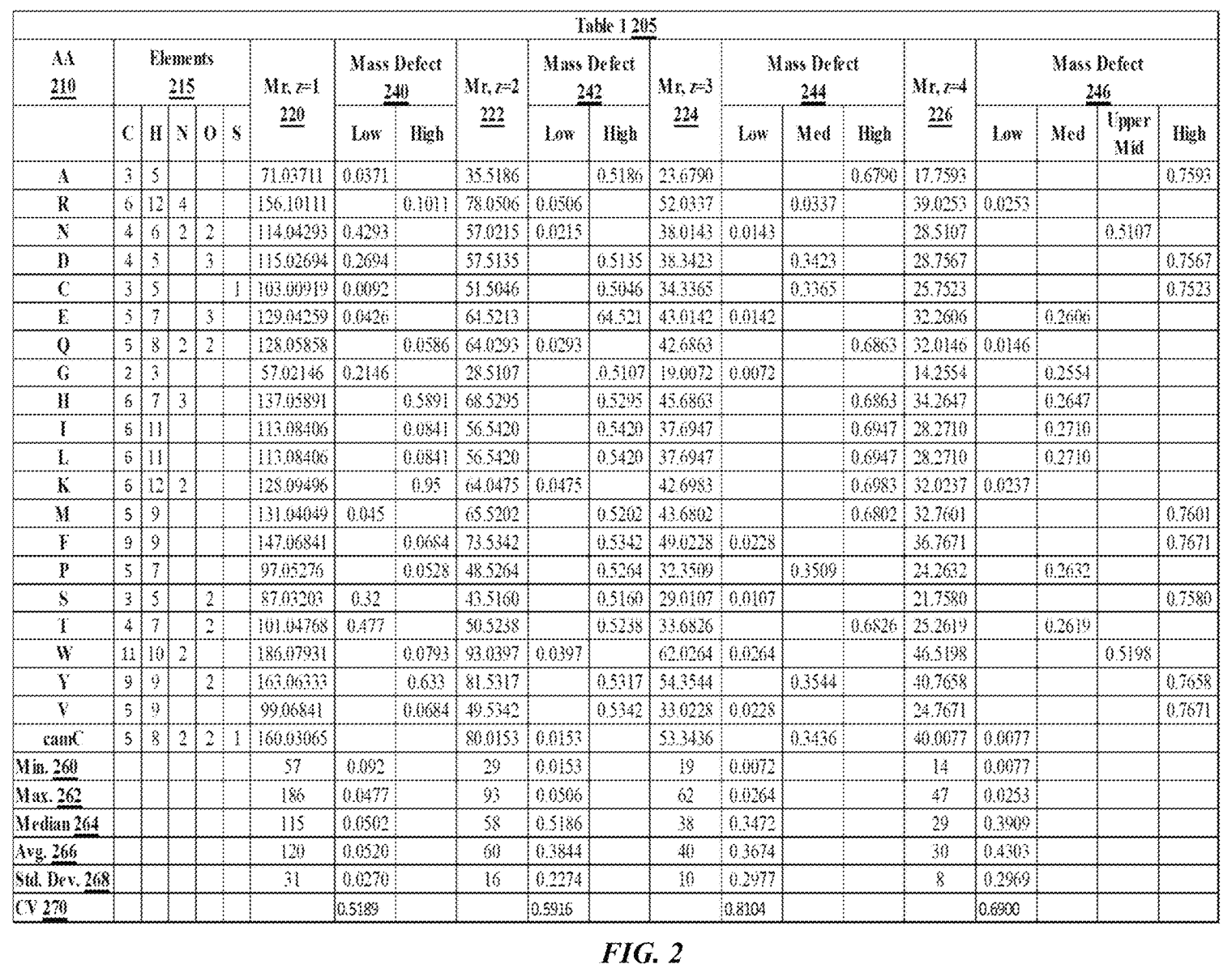

FIG. 2 depicts Table 1 205 providing mass information 144 for the constituent elements of a peptide precursor molecule. More specifically, FIG. 2 provides NM-MD mass information for the amino acids 210 (with cysteine modified by carboxyaminomethylation), which includes, without limitation, the elemental makeup 215 of each amino acid, the molecular mass ($M_r$) at the charge states of z=1 220, z=2 222, z=3 224, and z=4 226, and the mass defect 240, 242, 244, and 246 at each charge state. As depicted in Table 1 205, minimum 260, maximum 262, median 264, average 266, standard deviation 268, and CV 270 values exist for both $M_r$ 220, 222, 224, and 226 and mass defect 240, 242, 244, and 246. Table 1 205 represents non-weighted values for the constituent elements of a peptide precursor molecule.

MS data analysis logic 130, for example, via NM-MD logic 132, may use the integer and mass defect of the constituent building blocks of the target compounds relative to that of their parent molecules' intact molecular mass. In some embodiments, given the m/z and z of the precursor ion(s) are known, the maximum charge reduced (1 charge at a time) m/z value(s) of the highest m/z product ion are known. In some instances, a single eluting component when ionized can exist at multiple charge states. For those components of multiple charge states each charge state is treated separately in both DDA and high-definition mass spectrometry (HDMS or HDMS$^E$)DIA acquisitions. Though the eluting component is singular in the liquid phase, when ionized it may exist at multiply charge states. In DDA acquisitions the charge states are separated by the mass isolation window. In HDMSE DIA acquisitions, the ion mobility separation (IMS), which is internal to the ion path, separates the charge states by their collisional cross-sectional area (CCSA$^2$). For MSE and SWATH type DIA acquisitions, both charge states will fragment simultaneously producing a product ion spectra containing both 2+ and 1+ fragment ions. Current precursor selection schemes based on DDA and/or DIA involve processes where fragmentation mass candidates are selected by intensity and are included in an exclusion directory to avoid constant refragmentation of highly abundant species. Conventional DDA and/or DIA methods do not fully utilize valuable information available based on the fractional mass of high-accuracy precursor mass measurements delivered by current instrumentation. Accordingly, the MS data analysis process according to some embodiments may, among other things, separate the product ions by charge state using one set of product ions to validate the other.

When a peptide bond is dissociated, two fragment ions are generated, Y-ions and B-ions (the compliment to the Y-ion). More particularly, if a peptide fragments at the peptide bond, then if a charge is retained on the N terminal fragment, that fragment ion is termed a B-ion. If the charge is retained on the C terminal fragment, the fragment ion is termed a Y-ion. A more comprehensive list of possible fragments and their nomenclature is provided in Roepstorff and Fohlman, Biomedical Mass Spectrometry, 1984; 11(11):601, and Johnson et al, Anal. Chem. 1987, 59(21): 2621:2625, both of which are hereby incorporated by reference. The fragment containing only the amino terminal amino acid is termed $b_1$, the fragment containing the first two amino terminal amino acids is termed $b_2$, and so forth.

The highest m/z product ion in an MS/MS spectrum from a precursor of charge z is referred to as $Y_{max}$, in which $Y_{max}=[M_r+(z-1)*H]/z$, where $M_r$ is the molecular mass of the precursor, z is the charge number of the precursor, and H is the mass of hydrogen. The maximum fragment ion mass for a B-ion is $B_{max}=[(M_r+(z-1)*H)-H_2O]/z$, where $M_r$ is the molecular mass of the precursor, z is the charge number of the precursor, H is the mass of hydrogen, and $H_2O$ is the molecular mass of water.

In some embodiments, NM-MD logic 132 may be operative to generate, access, and/or provide NM-MD relationship information 146. In various embodiments, NM-MD relationship information 146 may include associations between the nominal m/z and the fractional m/z of elements associated with a target precursor, such as product ion fragments. In exemplary embodiments, NM-MD relationship information 146 may include a determination of nominal m/z and the fractional m/z for product ion fragments, such as represented in FIGS. 4-7. For example, FIGS. 4-7 represent a density plot or graph of nominal m/z and the fractional m/z for product ion fragments of certain z values. In some embodiments, the product ion fragments depicted in FIGS. 4-7 may be a result of empirical mass analysis via a MS. In other embodiments, the product ion fragments depicted in FIGS. 4-7 may be the result of in silico digests or graphical representations of other computer-generated data (for instance, UniProt and/or the like).

Figure 4:
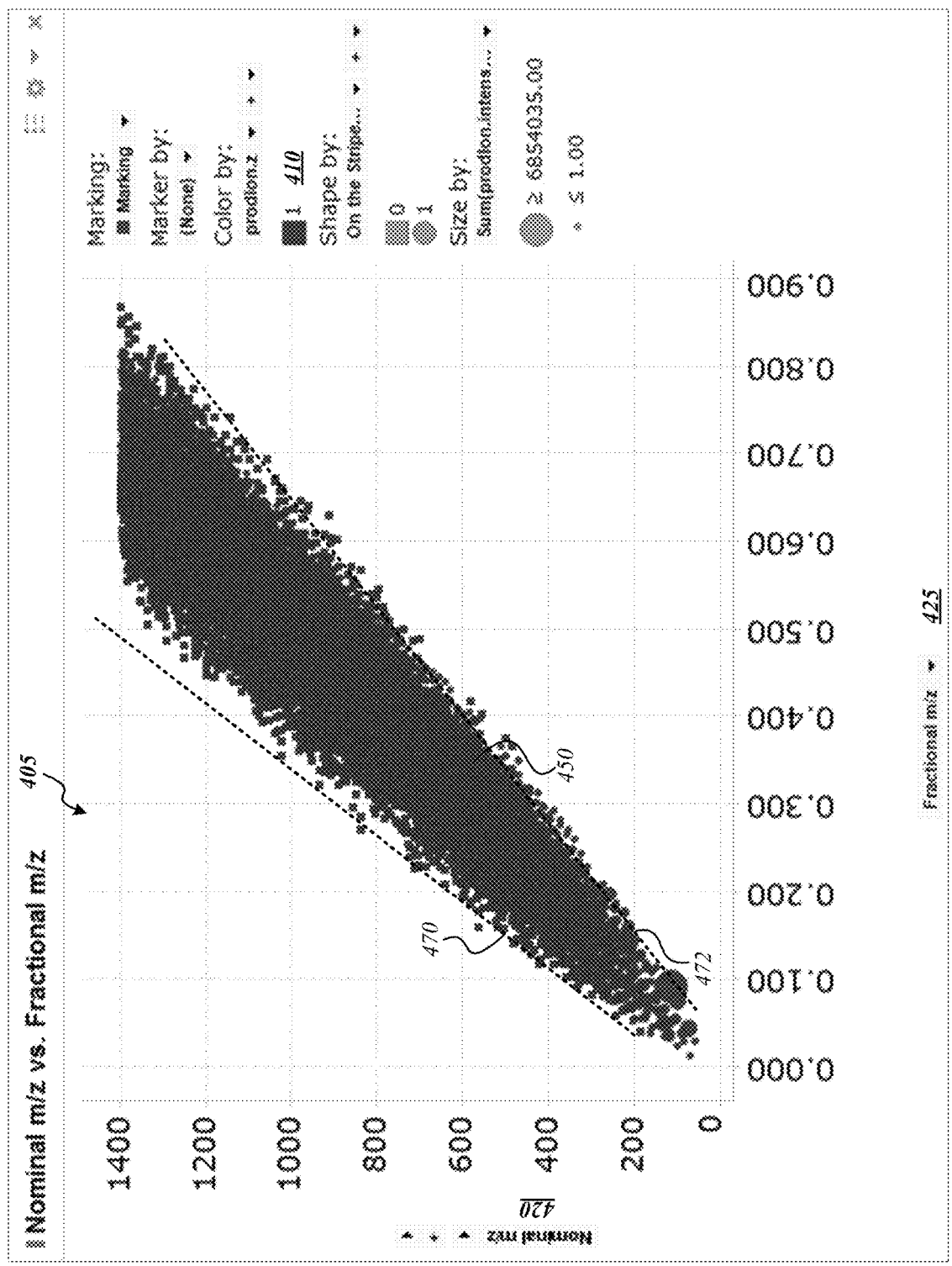
FIG. 4 depicts a graph of nominal mass versus fractional mass for ions of z=1.
Figure 5:
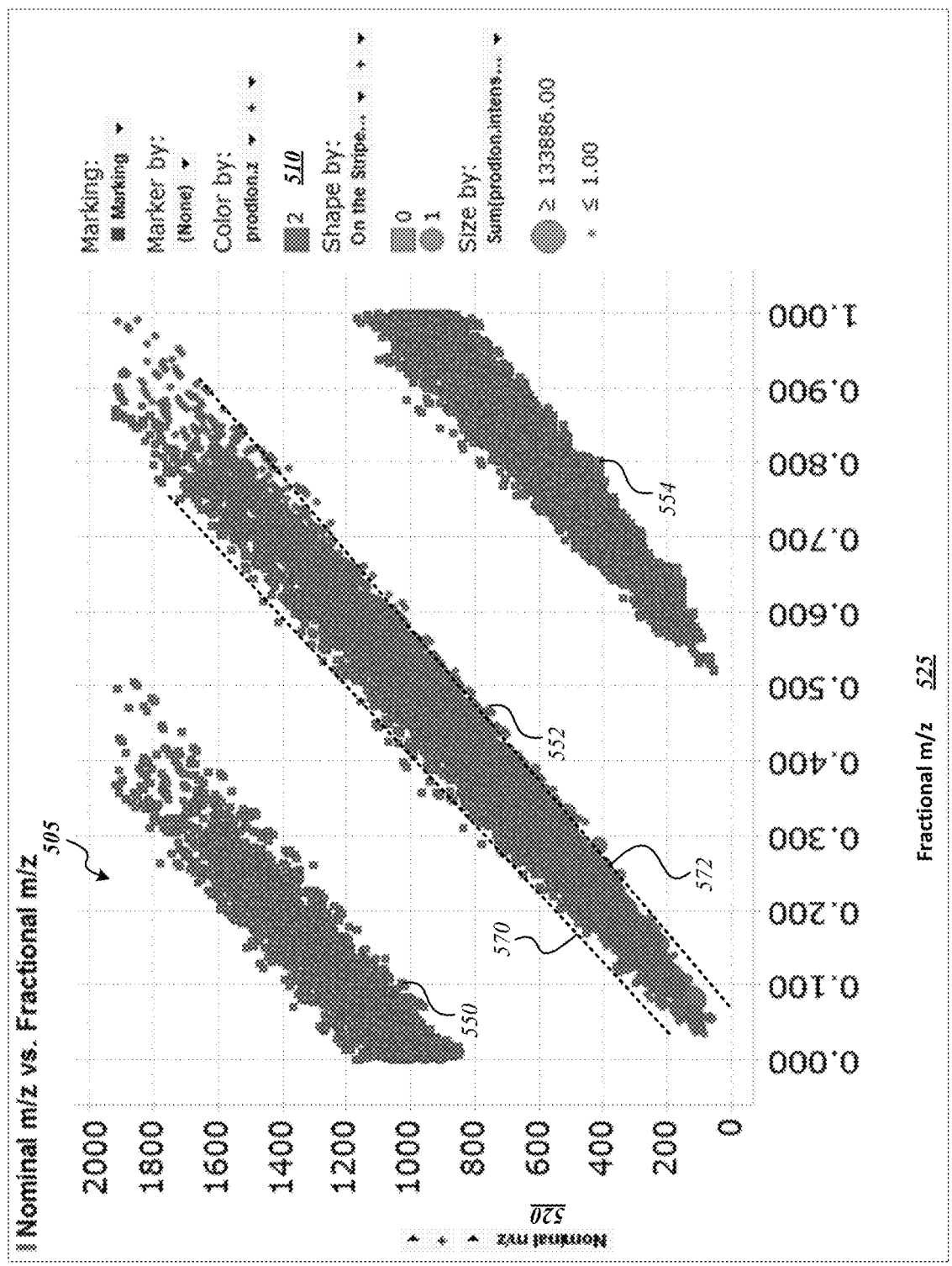
FIG. 5 depicts a graph of nominal mass versus fractional mass for ions of z=2.
Figure 6:
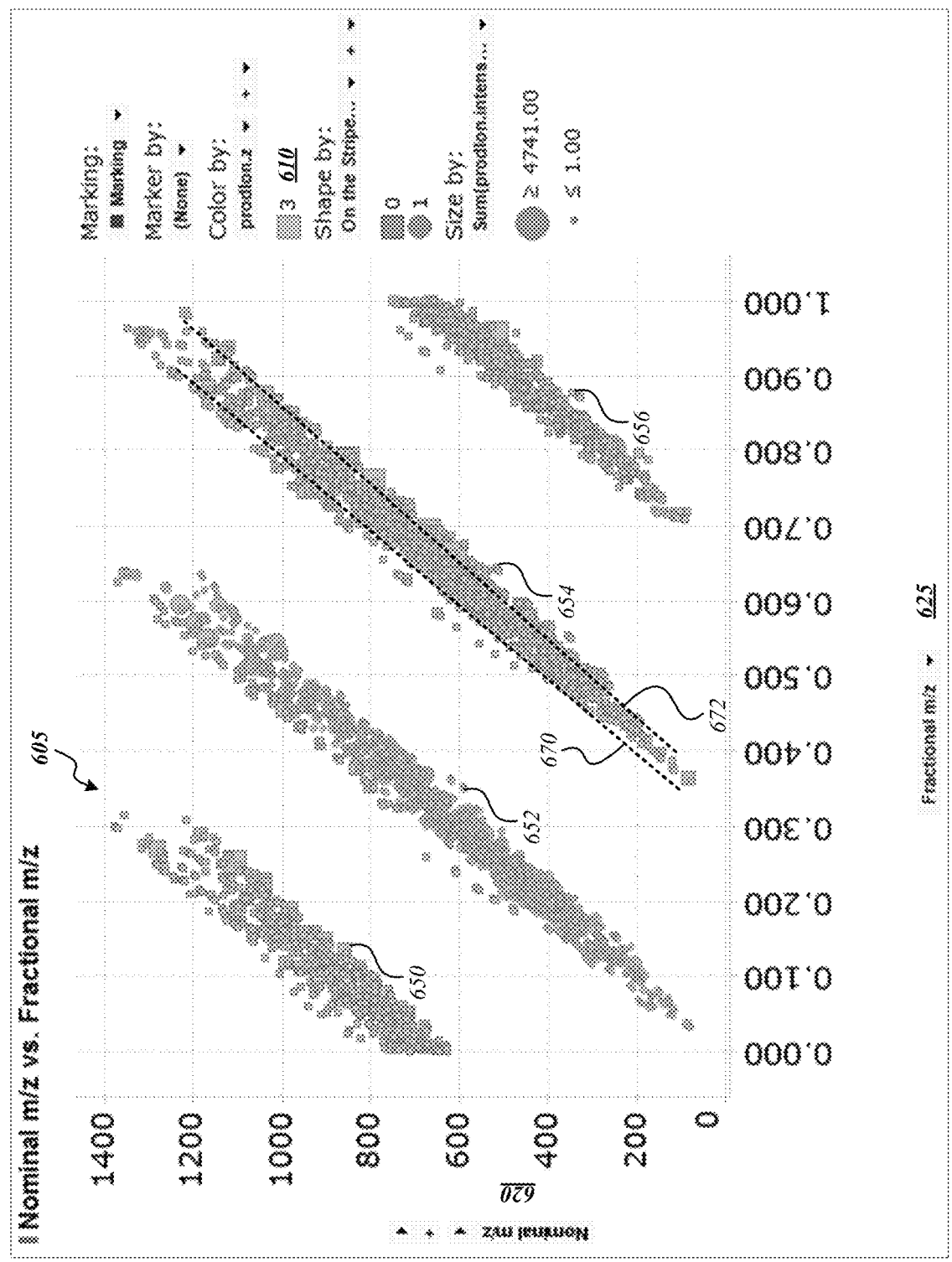
FIG. 6 depicts a graph of nominal mass versus fractional mass for ions of z=3.
Figure 7:
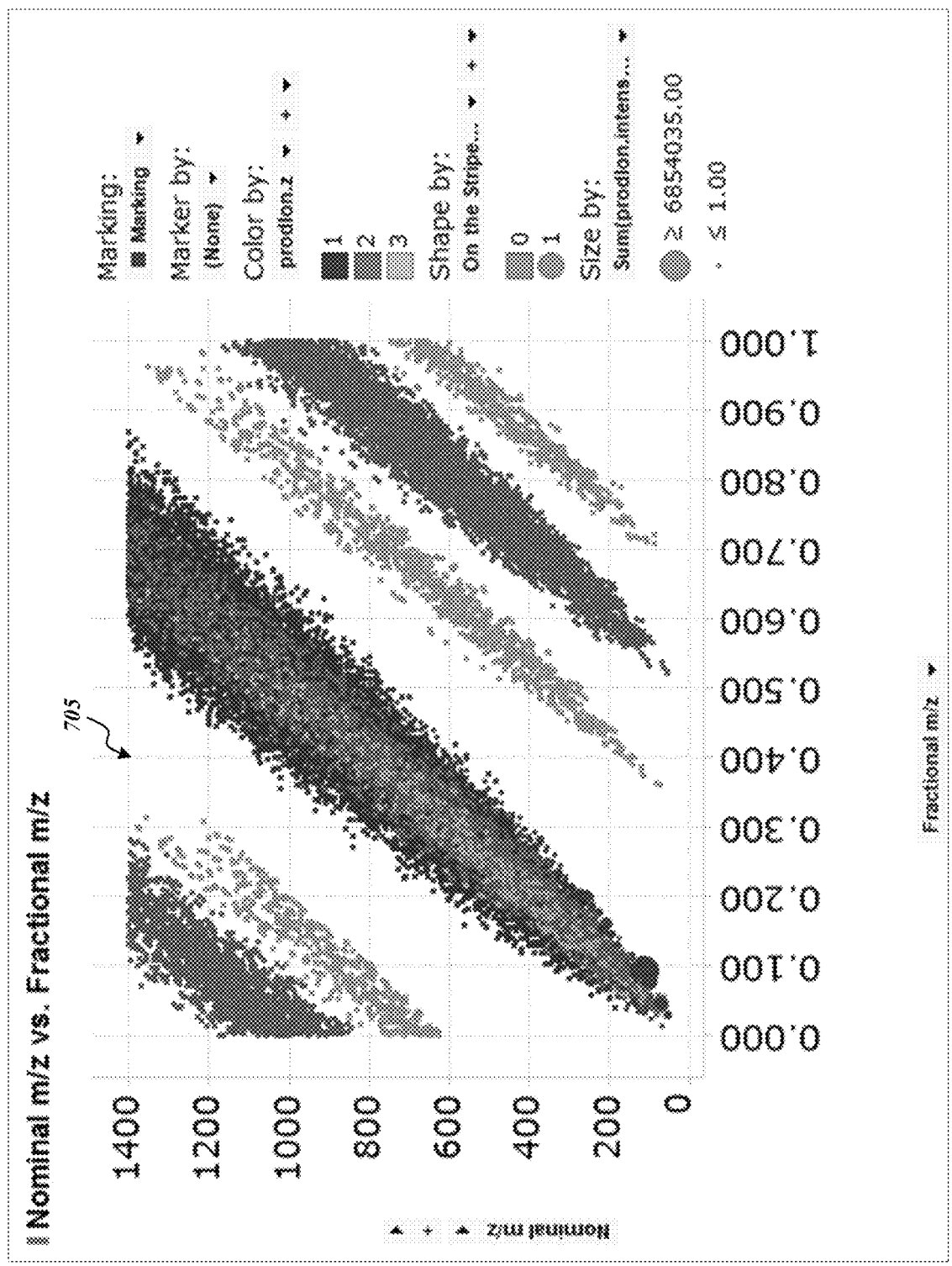
FIG. 7 depicts a graph of nominal mass versus fractional mass for ions of z=1-3.

FIG. 4 depicts NM-MD relationship information 146 in the form of a graph 405 or plot representing nominal m/z 420 versus fractional m/z 425 for ions, such as product ions, of z=1 410. As shown in FIG. 4, plot 405 may include a single charge vector 450 of product ions. FIG. 5 depicts NM-MD relationship information 146 in the form of a graph 505 representing nominal m/z 520 versus fractional m/z 525 for ions of z=2 510. As shown in FIG. 5, plot 505 may include a plurality of charge vectors 550, 552, and 554 of product ions. FIG. 6 depicts NM-MD relationship information 146 in the form of a graph 605 representing nominal m/z 620 versus fractional m/z 625 for ions of z=3 610. As shown in FIG. 6, plot 605 may include a plurality of charge vectors 650, 652, 654, and 656 of product ions. FIG. 7 depicts NM-MD relationship information 146 in the form of a combined density graph 705 for ions of z=1-3.

In various embodiments, NM-MD logic 132 may be operative to select candidate product ion fragments from the population of potential product ion products associated with a sample, target precursor(s), or class of compound (for instance, peptides). In exemplary embodiments, the MS data analysis process may provide precursor and product ion alignment using generated relationships associated with the nominal mass and mass defect of a precursor ions (for example, [Mr+(z−1)*H]/z) and that of its principal product ions. For instance, as the target precursor molecule fragments, each fragment may decrease in both nominal mass and mass defect by the nominal mass and mass defect of the constituent component (building block) of the parent. For example, an MS data analysis process according to some embodiments may calculate a weight averaged nominal mass and mass defect as well as standard deviations of each from the set of building blocks of the molecules understudy.

FIG. 3 depicts Table 2 305 providing mass information 144 in the form of constituent element distribution information. For peptides, mass information 144 may be in the form of an average frequency distribution 315 of amino acids 310 in the proteomes of yeast, human and mouse. In some embodiments, average frequency distribution 315 may be used to determine the weight averaged median nominal and fractional mass values for a sample containing peptides.

Figure 8:
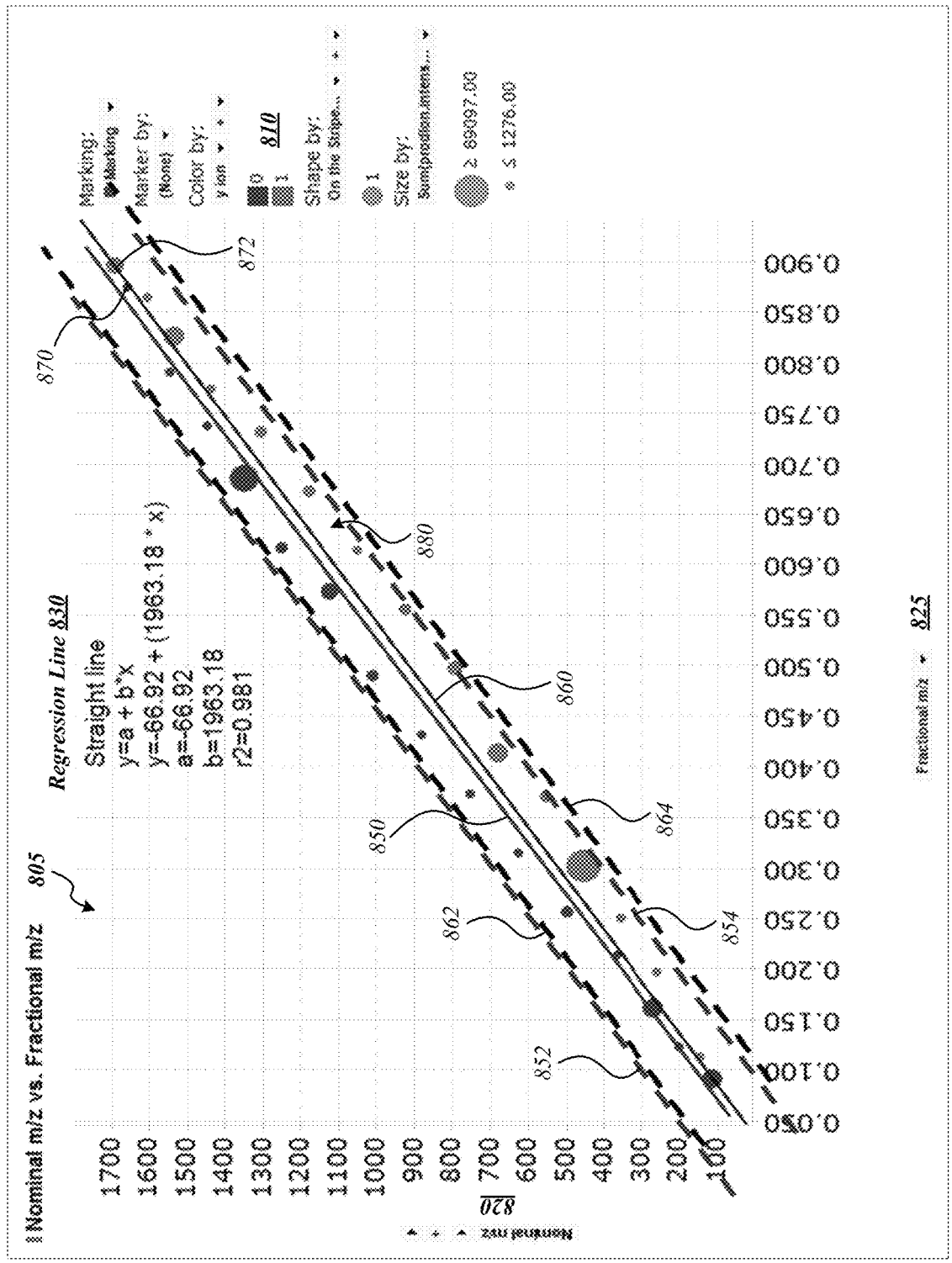
FIG. 8 depicts a graph illustrating regression line fits according to some embodiments.

An MS data analysis process configured according to some embodiments may use the nominal and mass defect of both $Y_{max}$ and $B_{max}$ as the maximum values, and the weight average nominal and mass defect of $Y_1$ and $B_1$, respectively, as the minimums to create two separate linear regression line fits for NM-MD relationship information (see, for example, FIG. 8). In some embodiments, the $Y_1$ and $B_1$ values may be held constant for all regression line fits. In acquisitions employing IMS, product ions may be pre-filtered, for example, by comparison of their nominal drift time to that of each parent precursor. Elimination by drift time is not absolute as the method employs an isolation window the width which is dictated by an adaptable function reflecting the precursor ion m/z and z values. Accordingly, the width of the isolation window increases as the m/z and z increase. In various embodiments, upper and lower boundary lines may be provided for each of the regression line fits for product ion extraction by adding either a user- or algorithmically-derived multiple of the respective standard deviations for both the nominal mass and mass defect of the constituent building blocks resident in the mass information 144 (for instance, FIG. 2, Table 1 205). In exemplary embodiments, all or substantially all product ions outside the upper and lower boundary lines are removed for consideration in the next stage of processing.

FIG. 8 depicts regression line fits according to some embodiments. As shown in FIG. 8, product ions may be plotted on a graph 805 of nominal m/z 820 versus fractional m/z 825, including $B_{max}$ ($[(Mr+(z-1)*H)-H_2O]/z$) 872 and $Y_{max}$ ($(M_r+(z-1)*H]/z$) 870. A first regression line fit 850 and a second regression line fit 860 are provided according to some embodiments. First regression line fit 850 may be associated with upper and lower boundaries 852 and 854, which are a threshold distance from first regression line fit 850. Second regression line fit 860 may be associated with upper and lower boundaries 862 and 864, which are a threshold distance from second regression line fit 860. Values of regression line 830 are also depicted in FIG. 8. According to some embodiments, the MS data analysis process may locate $Y_{max}$ and $Y_1$ on the graph 805 and generate a line connecting $Y_{max}$ and $Y_1$ to generate one regression line fit 860. In some embodiments, the MS data analysis process may locate $B_{max}$ and $B_1$ on the graph 805 and generate a line connecting $B_{max}$ and $B_1$ to generate another regression line fit 850. In some embodiments, the threshold distance may include a standard deviation used to determine the upper and lower boundaries 852, 854, 860, 864, which may be based on the integer mass and mass defect of a constituent element, such as tryptophan. In some embodiments, the threshold distance may be a manual- or algorithmic-based value. In some embodiments, regression line fit 850 may represent a maximum regression line fit and regression line fit 860 may represent a minimum regression line fit. Referring to FIGS. 4-8, therein are depicted regression line fits for the ions depicted therein, including regression line fits 470 and 472 for FIG. 4, regression line fits 570 and 572 for FIG. 5, and regression line fits 670 and 672 for FIG. 6.

As shown in FIG. 8, Y-ions are predominately below the regression line fit(s) whereas B-ions are predominately (>98.2%) above. Accordingly, MS data analysis processes according to some embodiments may provide increased selectivity in the identification process by allowing Y-ions to be segregated from the B-companions. Product ions between the regression line fit upper and lower boundaries 852 and 854 and/or regression line fit upper and lower boundaries 862 and 864 may be selected and designated as candidate ion fragments.

The process of selecting and designating candidate ion fragments may be replicated for charge values of interest. For example, the process of determining regression line fits (and their respective upper and lower boundaries) for charge vectors may be repeated for precursor ions of z>2. For certain fragmentation processes, such as collision-induced dissociation (CID), precursor ions of z>2 can produce fragment ions from 1+ to a maximum of z−1. Extraction of the 1+ complement of fragment ions may be performed as depicted for FIG. 8. Eue to the elemental composition of amino acids and the ability of peptide ions to exist at multiple charge states in a MS, some of the higher z fragment ions will be captured in the 1+ processing. For 2+ product ions, those that do not fall within the 1+ upper and lower boundary lines, their mass defects will toggle between an upper and lower charge vector. FIG. 5 illustrates in 2-dimensional space the nominal mass 520 versus mass defect 525 of the 2+ product ions where the center charge vector 552 is within 1+ upper and lower boundary lines the other isotopes are distributed within the upper charge vector 550 and lower charge vector 554. Referring to Table 1 205, therein is depicted the toggling in fraction mass between the three charge vector lanes.

In some embodiments, the regression line fits for the upper and lower charge vector lanes are calculated using [Mr+(z−1)*H]/z as the maximum and the median weight averaged $B_1$ and $Y_1$ [Mr+(z−1)*H]/z for the minimum for precursor ions of z>2. The upper charge vector may be calculated using the [Mr+(z−1)*H]/z of the precursor as the maximum and the median weight averaged $B_1$ and $Y_1$ [Mr+(z−1)*H]/z for the minimum. The lower charge vector may be calculated similarly; however, the maximum value may be set to the precursor ion's [Mr+(z−1)*H]/z minus 1× the median nominal and mass defect from the mass information of the constituent building blocks (for instance, Table 1 205). In various embodiments, the minimal nominal mass and mass defect may be identical to the upper charge vector. The number of unique charge vector lanes is proportional to (z−1) for precursor ions of z>2. Higher z precursor ions may be processed similarly. For example, FIG. 6 depicts the 3+ precursor ion charge vector lanes.

Once all regression line fits have been constructed, the MS analysis process according to some embodiments may create a stripe (in 2- or 3-dimensional space), depending on whether IMS was employed, selecting only the candidate product ions that were captured between the upper and lower boundary lines of their respective regression line fits. The stripe, such as the candidate ions of the stripe 880 of FIG. 8, is defined by upper and lower boundary lines. These boundary lines reflect the theoretical values plus/minus standard deviations for each of the two values, nominal mass and mass defect. These widths (or number of standard deviations) in the 2 dimensions of nominal mass and mass defect project a stripe of candidate ion fragments above and below the regression line fit. Ions that are not within the stripe of candidate ions may be removed from further consideration and/or analysis of the target precursor or potential fragment ions.

Once the candidate ion fragments on the stripe are extracted, the fragmentation efficiency logic 134 may be operative to perform a fragmentation filtering process of the MS data analysis process. In some embodiments, the fragmentation filtering process may be operative to further filter the candidate ion fragments based on the fragmentation efficiency to determine target ion fragments. In some embodiments, fragmentation efficiency may be determined as 1 minus the ratio of the residual ion intensity/precursor ion intensity. In various embodiments, sensitivity as a function of qualitative analysis directly relates to fragmentation efficiency. For example, too much residual precursor ion intensity in the MS/MS spectrum indicates poor fragmentation and, therefore, lower intensity product ions. Similarly, the absence of any residual precursor ion intensity in the MS/MS spectrum, provided the precursor ion cluster intensity is high enough to produce a statistically significant number of product, may indicate over-fragmentation. In exemplary embodiments, the identification of constituent components across the widest dynamic range is a function of product ion intensity.

Figure 9:
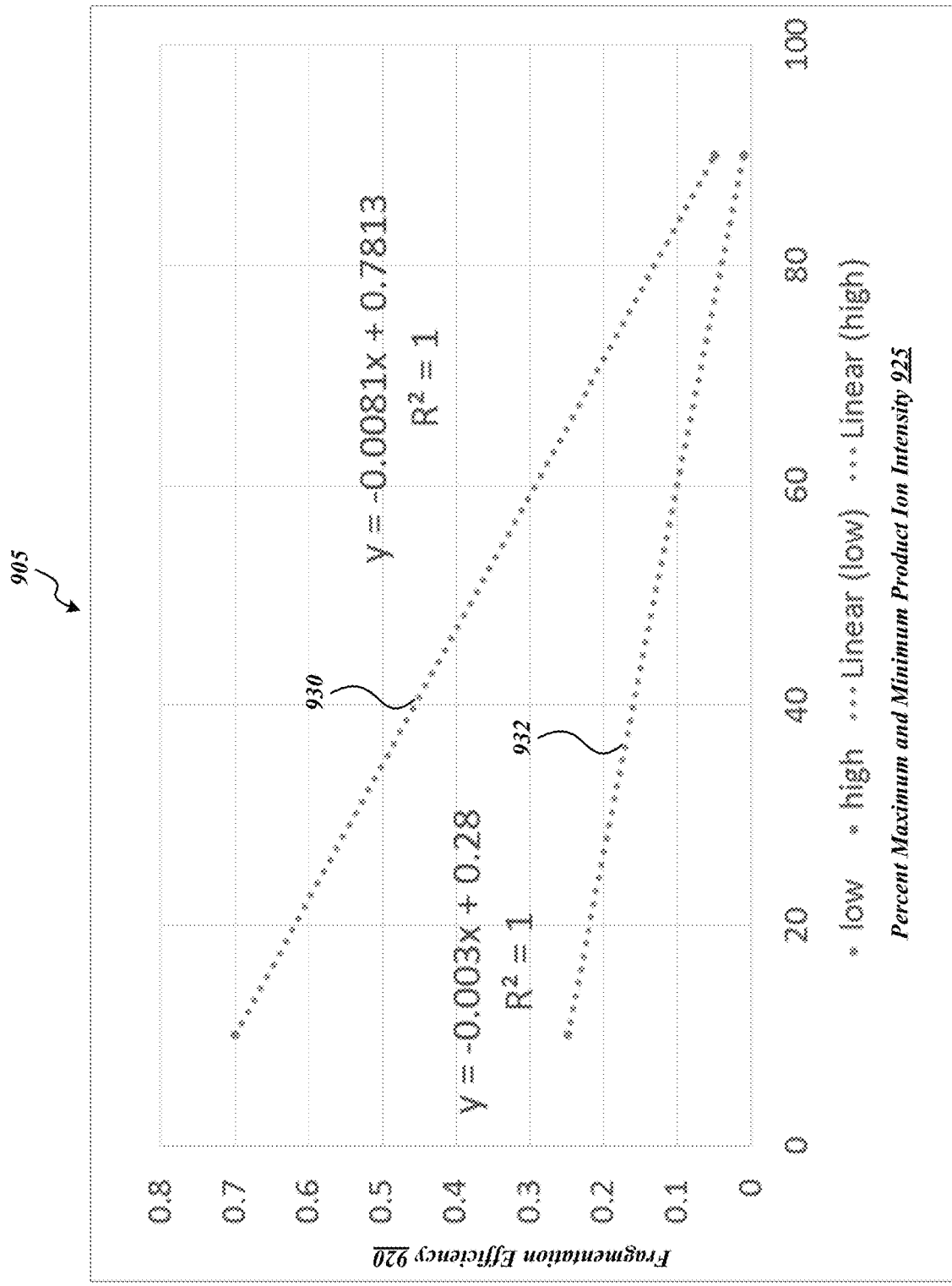
FIG. 9 depicts a graph of fragmentation efficiency versus percent maximum and minimum product ion intensity.

The fragmentation filtering process according to some embodiments determines the residual precursor ion cluster in the product ion spectrum and calculates the difference in their respective intensities to calculate the fragmentation efficiency. FIG. 9 depicts a graph 905 of fragmentation efficiency 920 versus percent maximum and minimum product ion intensity 925. In some embodiments, the calculated fragmentation efficiency may be compared to FIG. 9, for example, and the maximum product ion intensities tolerance 930 and minimum product ion intensities tolerances 932 relative to the precursor ions are set. In some embodiments, FIG. 9 may be generated by statistical analysis of a set of previously acquired data sets, such as DDA data sets and/or simulated data sets. DDA data sets may be used because the instrument uses a lookup table of optimized collision energy values for each switched on precursor ion's nominal mass and z. The collision energy may be varied from the optimal settings to characterize the fragmentation efficiency. From these datasets, the regression line fits for the upper (most intense product) and lower (least intense product) boundary lines may be calculated based on the precursor ion's fragmentation efficiency.

Figure 10A:
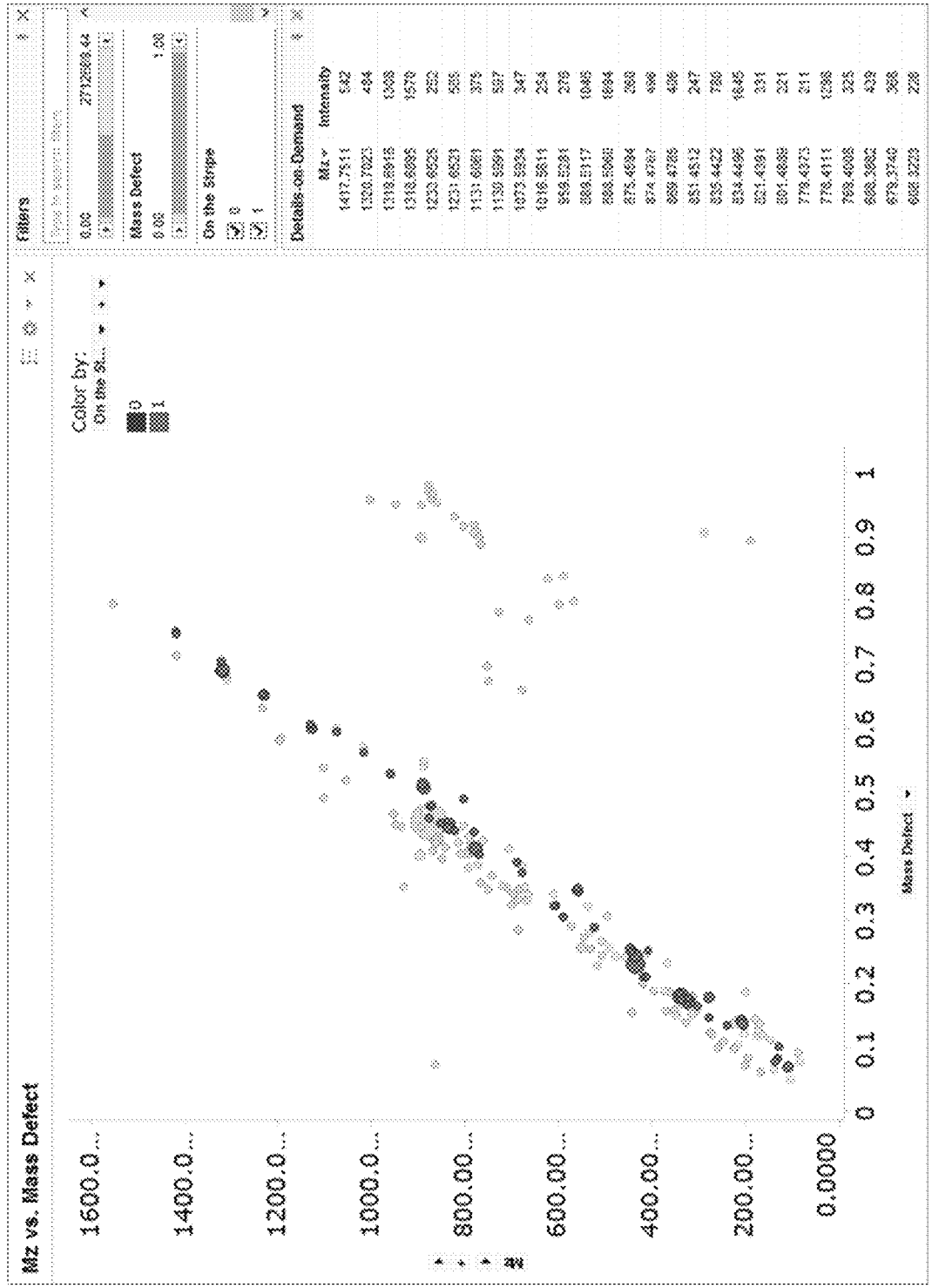
FIG. 10A depicts a graph of nominal mass versus fractional mass for potential product ions.
Figure 10B:
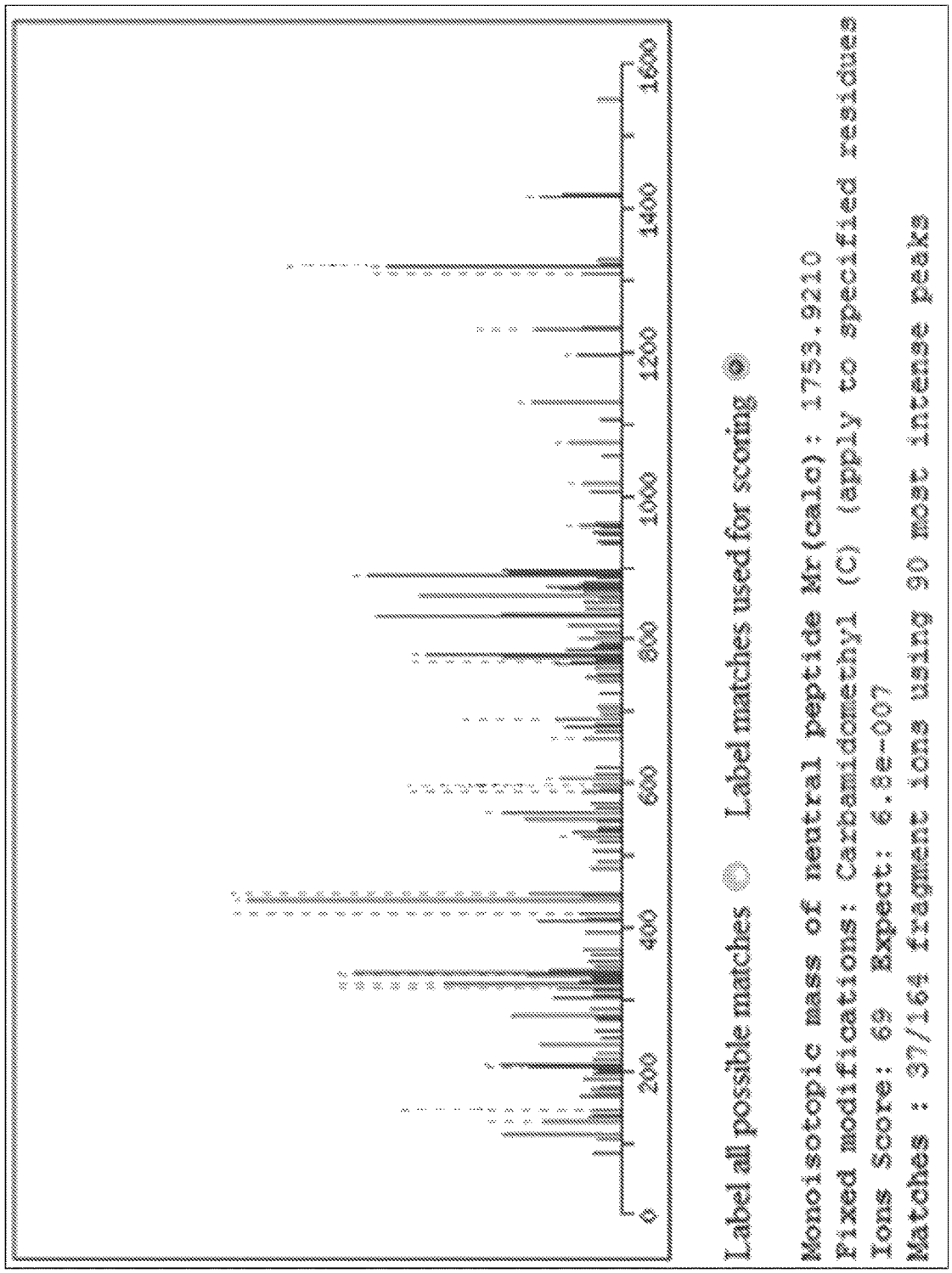
FIG. 10B depicts a mass spectrum of the product ions of the graph of FIG. 10A.
Figure 11A:
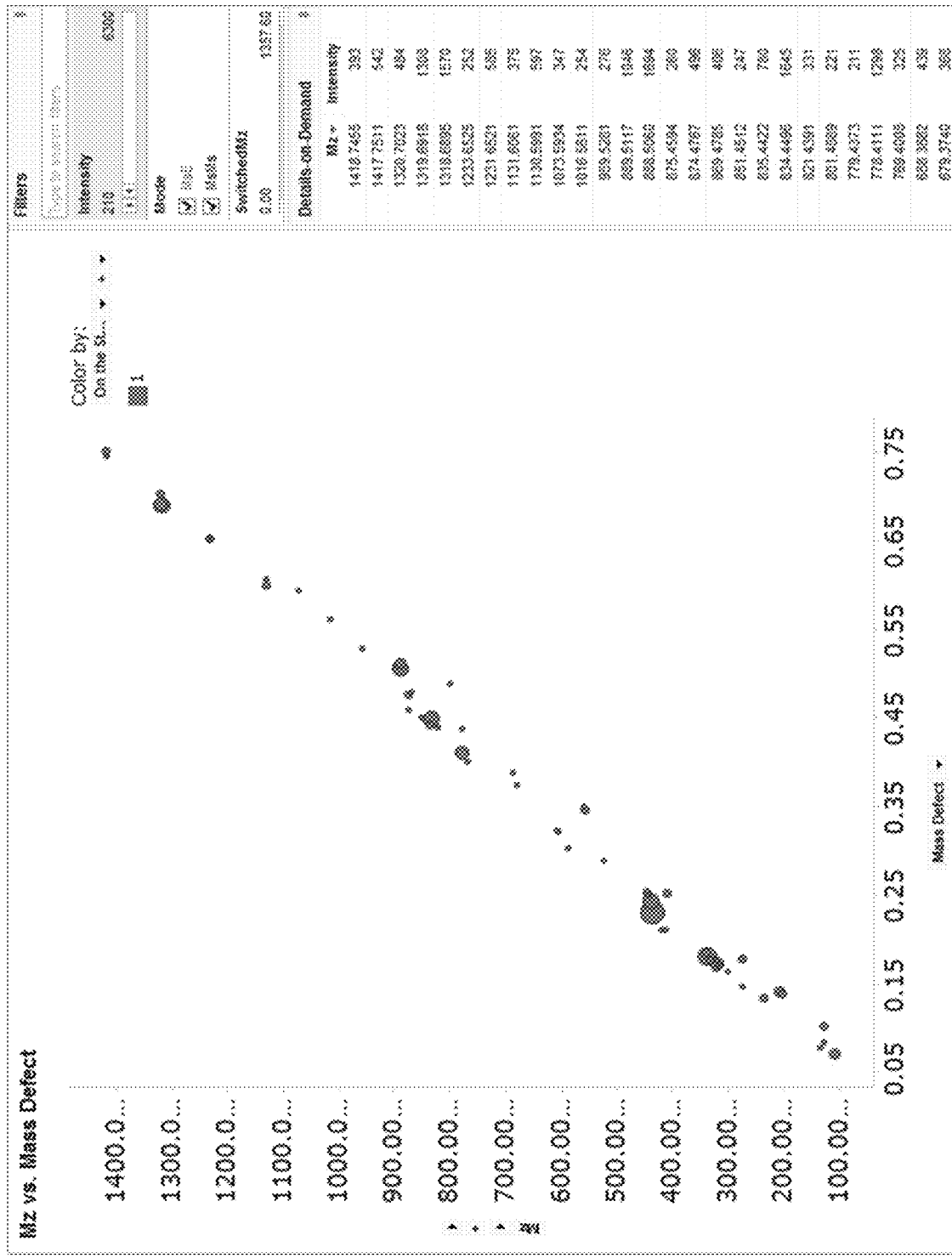
FIG. 11A depicts a graph of nominal mass versus fractional mass for target product ions.
Figure 11B:
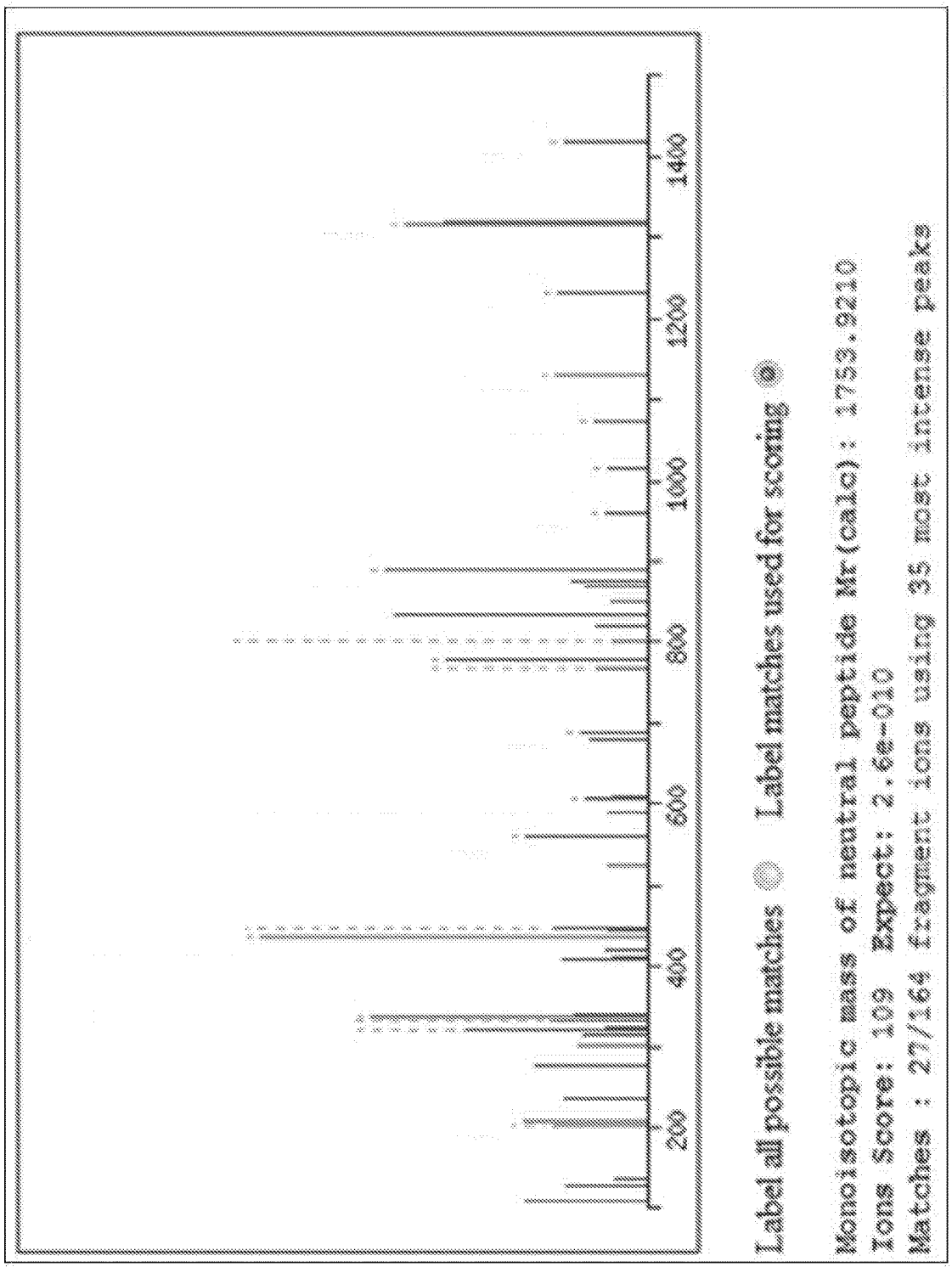
FIG. 11B depicts a mass spectrum of the target product ions of the graph of FIG. 11A.

FIGS. 10A and 11A depict nominal mass versus mass defect for potential product ions of interest for a target precursor. FIG. 10A depicts potential product ions that have not been filtered according to some embodiments; rather, they are unfiltered or filtered according to conventional methods. FIG. 11A depicts (a stripe of) target fragment ions that were located on a charge vector strip between the upper and lower bounds of nominal mass and mass defect and within the intensity windows of the upper and lower intensity bounds. FIGS. 10B and 11B depict spectra generated from the ion data sets based on the target fragment ions of FIGS. 10A and 11A, respectively, labeled by z value and fragment ion type (Y-ion or B-ion). The spectrum of FIG. 10B includes significantly more peaks than the spectrum of FIG. 11B. Accordingly, precursor-product analysis and/or alignment may be more efficient and accurate using the filtered spectrum of FIG. 11B. For example, the peptide match or "ions score" for FIG. 10B is 69, while the ions score for FIG. 11B is 109, which is a significant improvement over the ions score for the conventional methods of FIG. 10B. In some embodiments, precursor-product alignment logic 136 may be operative to align product ion fragments with a target precursor, for example, using the ion data sets 142 and/or associated spectra, such as the spectra depicted in FIGS. 10B and 11B.

In some embodiments, the MS data analysis process may perform a de-novo sequencing process and/or a sequence tag formation process based on, among other things, fractional mass, nominal mass, z, and fragment ion type. A de-novo sequencing process may include determining the delta nominal mass between the precursor ions' [Mr+(z−1)*H]/z and its near Y-ion neighbors (below the regression line) within the maximum integer mass of all the constituent elements, for example, as provided in Table 1 205. Given a nominal mass match, the delta of the mass defects is compared to validate the match, if the match is made within a match tolerance or threshold, the attributes of the [Mr+(z−1)*H]/z are replaced with those of the matched product ion and the process may be repeated. In instances where there is no initial match (for example, no $Y_{max}$-1 amino acid), the algorithm looks for the delta nominal mass and mass defect of two amino acids in an attempt to connect to $Y_{max}$-2 amino acids. If no connection is made for $Y_{max}$-1 amino acid or $Y_{max}$-2 amino acids, the process takes the most intense product ion, knowing its fragment ion type (above b or below y), and subtracts its nominal mass from the precursor ion's [Mr+(z−1)*H]/z nominal mass and looks for the companion (upper/lower stripe) for its complementary pair. The process repeats this process until all the extracted product ions are queried for their complementary pair. If a complementary pair is found the [Mr+(z−1)*H]/z value from the first pass is replaced with that of the complementary pair and the same process is repeated lane-by-lane.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

A logic flow may be implemented in software, firmware, hardware, or any combination thereof. In software and firmware embodiments, a logic flow may be implemented by computer executable instructions stored on a non-transitory computer readable medium or machine readable medium, such as an optical, magnetic or semiconductor storage. The embodiments are not limited in this context.

FIG. 12 illustrates an embodiment of a logic flow 1200. Logic flow 1200 may be representative of some or all of the operations executed by one or more embodiments described herein, such as apparatus 120 and/or MS 110. In some embodiments, logic flow 1200 may be representative of some or all of the operations of a MS data analysis process.

Logic flow 1200 may determine a target precursor at block 1202. For example, an operator of MS 110 may enter at least one target precursor of interest (for instance, a protein or peptide) during analysis of a sample. At block 1204, logic flow 1200 may access precursor composition information for elements of the target precursor. For example, for a peptide target precursor, MS data analysis logic 130 may access mass information 144 that includes nominal mass and mass defect for multiple charge values for amino acids, such as provided in Table 1 205. Logic flow 1200 may determine NM-MD relationship information for ion fragments associated with the target precursor at block 1206. For example, NM-MD 132 may determine, generate, access, and/or provide plots of nominal m/z versus mass defect m/z for certain charge values, such as depicted in FIGS. 4-7.

At block 1208, logic flow 1200 may determine an ion fragment upper boundary and an ion fragment lower boundary for the ion fragments. For example, the MS data analysis process configured according to some embodiments may use the nominal and mass defect of both $Y_{max}$ and $B_{max}$ as the maximum values, and the weight average nominal and mass defect of $Y_1$ and $B_1$, respectively, as the minimums to create two separate linear regression line fits for NM-MD relationship information. In addition, upper and lower boundary lines may be provided for each of the regression line fits for product ion extraction by adding either a user- or algorithmically-derived multiple of the respective standard deviations for both the nominal mass and mass defect of the constituent building blocks resident in the mass information 144. At block 1210, logic flow 1200 may extract candidate ion fragments based on applying the ion fragment upper boundary and the ion fragment lower boundary to the NM-MD relationship information. For example, referring to FIG. 8, product ions between the regression line fit upper and lower boundaries 852 and 854 and regression line fit upper and lower boundaries 862 and 864 may be selected and designated as candidate ion fragments.

Figure 13:
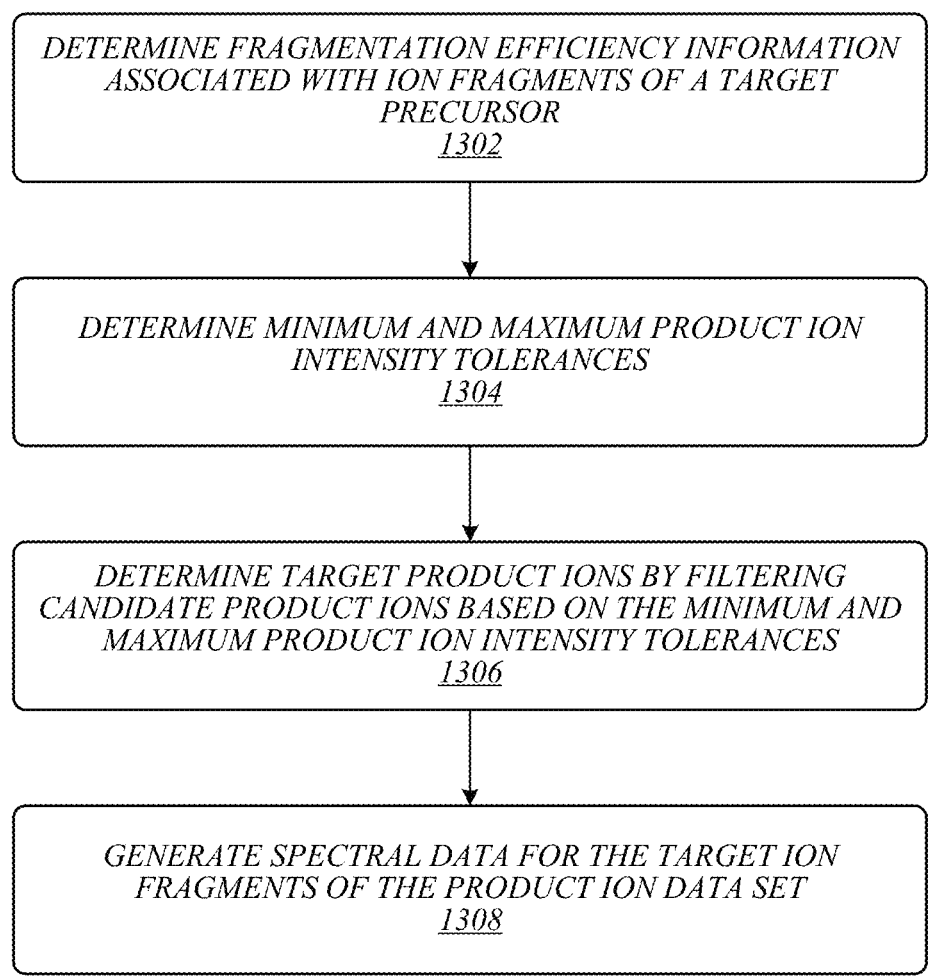
FIG. 13. illustrates an embodiment of a first logic flow.

FIG. 13 illustrates an embodiment of a logic flow 1300. Logic flow 1300 may be representative of some or all of the operations executed by one or more embodiments described herein, such as apparatus 120 and/or MS 110. In some embodiments, logic flow 1300 may be representative of some or all of the operations of a MS data analysis process.

Logic flow 1300 may determine fragment efficiency information associated with ion fragments of a target precursor at block 1302. For example, the fragmentation filtering process may be operative to further filter the candidate ion fragments based on the fragmentation efficiency to determine target ion fragments. In some embodiments, fragmentation efficiency may be determined as 1 minus the ratio of the residual ion intensity/precursor ion intensity. At block 1304, logic flow 1300 may determine minimum and maximum product ion intensity tolerances. For example, the calculated fragmentation efficiency may be compared to FIG. 9 for example, and the maximum product ion intensities tolerance 930 and minimum product ion intensities tolerances 932 relative to the precursor ions are set. Logic flow 1300 may determine target product ions by filtering candidate product ions based on the minimum and maximum product ion intensities at block 1306. For example, FIG. 11A depicts target fragment ions that were located on a charge vector strip between the upper and lower bounds of nominal mass and mass defect and within the intensity windows of the upper and lower intensity bounds. At block 1308, logic flow 1300 may generate spectral data for the target ion fragments of the product ion data set. For example, FIG. 11B depicts spectra generated from the ion data sets based on the target fragment ions of FIG. 11A labeled by z value and fragment ion type (Y-ion or B-ion).

Figure 14:
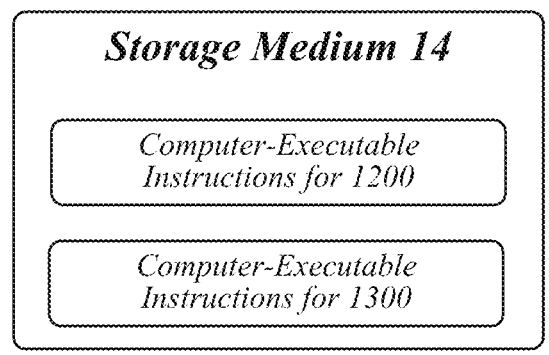
FIG. 14 illustrates an example of a storage medium.

FIG. 14 illustrates an example of a storage medium 1400. Storage medium 1400 may comprise an article of manufacture. In some examples, storage medium 1400 may include any non-transitory computer readable medium or machine readable medium, such as an optical, magnetic or semiconductor storage. Storage medium 1400 may store various types of computer executable instructions, such as instructions to implement logic flow 1200 and/or 1300. Examples of a computer readable or machine readable storage medium may include any tangible media capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like. The examples are not limited in this context.

Figure 15:
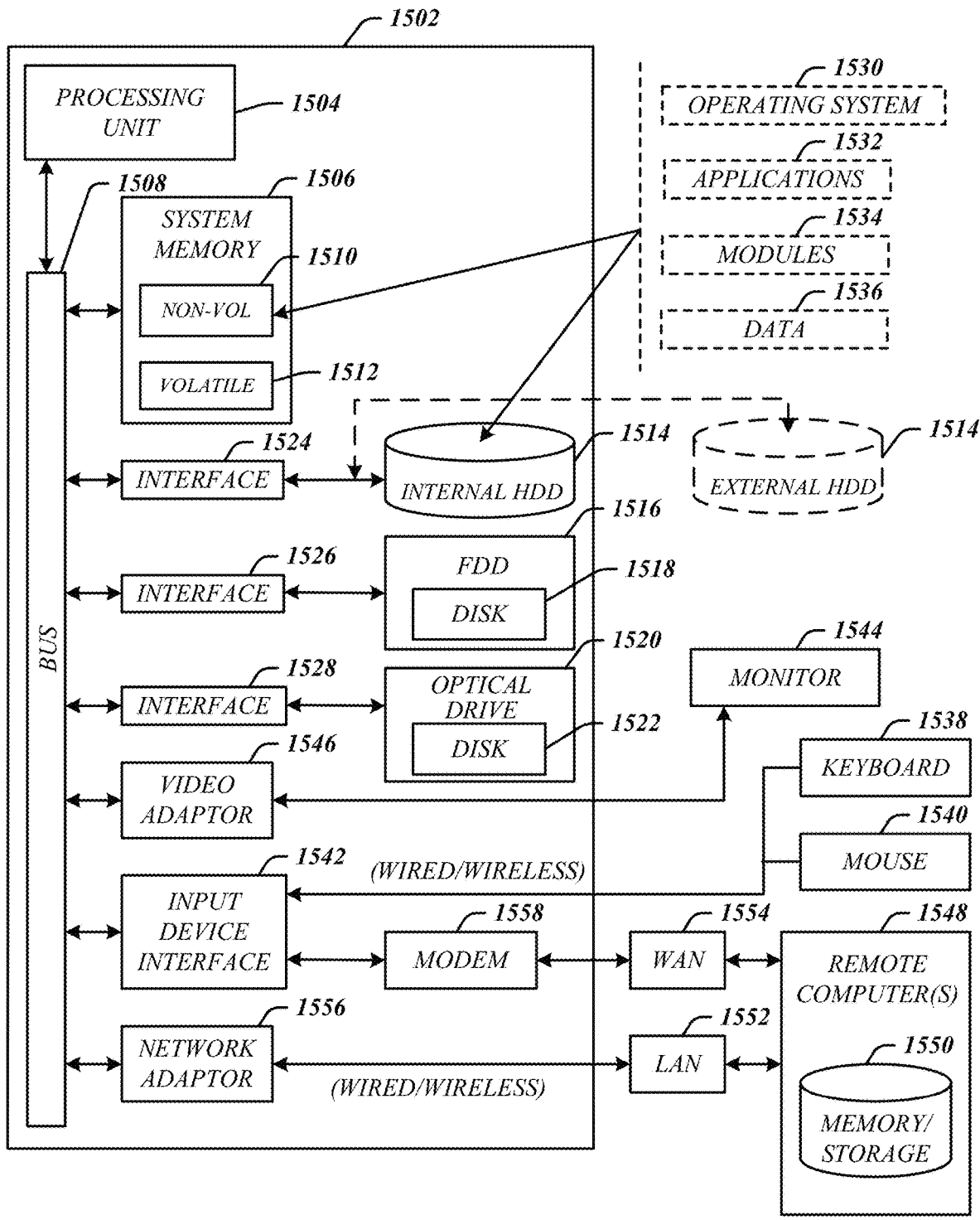
FIG. 15 illustrates an embodiment of a computing architecture.

FIG. 15 illustrates an embodiment of an exemplary computing architecture 1500 suitable for implementing various embodiments as previously described. In various embodiments, the computing architecture 1500 may comprise or be implemented as part of an electronic device. In some embodiments, the computing architecture 1500 may be representative, for example, of apparatus 120 and/or MS 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1500. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1500 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1500.

As shown in FIG. 15, the computing architecture 1500 comprises a processing unit 1504, a system memory 1506 and a system bus 1508. The processing unit 1504 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1504.

The system bus 1508 provides an interface for system components including, but not limited to, the system memory 1506 to the processing unit 1504. The system bus 1508 can be any of several types of bus structure that may further interconnect to a memory bus (with or without a memory controller), a peripheral bus, and a local bus using any of a variety of commercially available bus architectures. Interface adapters may connect to the system bus 1508 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1506 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 15, the system memory 1506 can include non-volatile memory 1510 and/or volatile memory 1512. A basic input/output system (BIOS) can be stored in the non-volatile memory 1510.

The computer 1502 may include various types of computer-readable storage media in the form of one or more lower speed memory units, including an internal (or external) hard disk drive (HDD) 1514, a magnetic floppy disk drive (FDD) 1516 to read from or write to a removable magnetic disk 1518, and an optical disk drive 1520 to read from or write to a removable optical disk 1522 (e.g., a CD-ROM or DVD). The HDD 1514, FDD 1516 and optical disk drive 1520 can be connected to the system bus 1508 by a HDD interface 1524, an FDD interface 1526 and an optical drive interface 1528, respectively. The HDD interface 1524 for external drive implementations can include at least one or both of Universal Serial Bus (USB) and IEEE 13154 interface technologies, among others.

The drives and associated computer-readable media provide volatile and/or nonvolatile storage of data, data structures, computer-executable instructions, and so forth. For example, a number of program modules can be stored in the drives and memory units 1510, 1512, including an operating system 1530, one or more application programs 1532, other program modules 1534, and program data 1536. In one embodiment, the one or more application programs 1532, other program modules 1534, and program data 1536 can include, for example, the various applications and/or components of apparatus 105 or MS 110.

A user can enter commands and information into the computer 1502 through one or more wire/wireless input devices, for example, a keyboard 1538 and a pointing device, such as a mouse 1540. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1504 through an input device interface 1542 that is coupled to the system bus 1508, but can be connected by other interfaces such as a parallel port, IEEE 1394 serial port, a game port, a USB port, an IR interface, and so forth.

A monitor 1544 or other type of display device is also connected to the system bus 1508 via an interface, such as a video adaptor 1546. The monitor 1544 may be internal or external to the computer 802. In addition to the monitor 1544, a computer typically includes other peripheral output devices, such as speakers, printers, and so forth.

The computer 1502 may operate in a networked environment using logical connections via wire and/or wireless communications to one or more remote computers, such as a remote computer 1548. The remote computer 1548 can be a workstation, a server computer, a router, a personal computer, portable computer, microprocessor-based entertainment appliance, a peer device or other common network node, and typically includes many or all of the elements described relative to the computer 1502, although, for purposes of brevity, only a memory/storage device 1550 is illustrated. The logical connections depicted include wire/wireless connectivity to a local area network (LAN) 1552 and/or larger networks, for example, a wide area network (WAN) 1554. Such LAN and WAN networking environments are commonplace in offices and companies, and facilitate enterprise-wide computer networks, such as intranets, all of which may connect to a global communications network, for example, the Internet.

When used in a LAN networking environment, the computer 1502 is connected to the LAN 1552 through a wire and/or wireless communication network interface or adaptor 1556. The adaptor 1556 can facilitate wire and/or wireless communications to the LAN 1552, which may also include a wireless access point disposed thereon for communicating with the wireless functionality of the adaptor 1556.

When used in a WAN networking environment, the computer 1502 can include a modem 1558, or is connected to a communications server on the WAN 1554, or has other means for establishing communications over the WAN 1554, such as by way of the Internet. The modem 1558, which can be internal or external and a wire and/or wireless device, connects to the system bus 1508 via the input device interface 1542. In a networked environment, program modules depicted relative to the computer 1502, or portions thereof, can be stored in the remote memory/storage device 1550. It will be appreciated that the network connections shown are exemplary and other means of establishing a communications link between the computers can be used.

The computer 1502 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

The following include non-limiting example embodiments:

Example 1 is a computer-implemented method of sample analysis, the method comprising accessing at least one product ion data set generated via mass analyzing a sample comprising at least one target precursor, accessing precursor composition information for a plurality of constituent elements of the at least one target precursor, the precursor composition information comprising nominal mass information and mass defect information for at least a portion of the plurality of constituent elements, determining nominal mass (NM)-mass defect (MD) relationship information for a plurality of ion fragments associated with the at least one target precursor based on the precursor composition information, determining at least one ion fragment upper boundary and at least one ion fragment lower boundary for the plurality of ion fragments, extracting a plurality of candidate ion fragments from the plurality of ion fragments via applying the at least one ion fragment upper boundary and the at least one ion fragment lower boundary to the NM-MD relationship information, and determining a plurality of target ion fragments from the plurality of candidate ion fragments based on fragmentation efficiency information associated with the plurality of candidate ion fragments.

Example 2 is the method of Example 1, comprising generating spectral data for the plurality of target ion fragments.

Example 3 is the method of Example 1, the at least one target precursor comprising a peptide and the plurality of constituent elements comprising amino acids.

Example 4 is the method of Example 1, the NM-MD relationship information comprising a graph of nominal mass versus mass defect for the plurality of ion fragments.

Example 5 is the method of Example 1, the at least one fragment lower boundary comprising a first regression line fit, a first upper boundary, and a first lower boundary a threshold distance from the first regression line fit.

Example 6 is the method of Example 5, the first regression line fit comprising a line fit between a $Y_{max}$ ion and a $Y_1$ ion.

Example 7 is the method of Example 6, the at least one fragment lower boundary comprising a second regression line fit, a second upper boundary, and a second lower boundary a threshold distance from the first regression line fit.

Example 8 is the method of Example 7, the second regression line fit comprising a line fit between a $B_{max}$ ion and a $B_1$ ion.

Example 9 is an apparatus operative to perform sample analysis, the apparatus comprising a processing circuitry, and logic, coupled to at least one memory, to access at least one product ion data set generated via mass analyzing a sample comprising at least one target precursor, access precursor composition information for a plurality of constituent elements of the at least one target precursor, the precursor composition information comprising nominal mass information and mass defect information for at least a portion of the plurality of constituent elements, determine nominal mass (NM)-mass defect (MD) relationship information for a plurality of ion fragments associated with the at least one target precursor based on the precursor composition information, determine at least one ion fragment upper boundary and at least one ion fragment lower boundary for the plurality of ion fragments, extract a plurality of candidate ion fragments from the plurality of ion fragments via applying the at least one ion fragment upper boundary and the at least one ion fragment lower boundary to the NM-MD relationship information, and determine a plurality of target ion fragments from the plurality of candidate ion fragments based on fragmentation efficiency information associated with the plurality of candidate ion fragments.

Example 10 is the apparatus of Example 9, the logic to generate spectral data for the plurality of target ion fragments.

Example 11 is the apparatus of Example 9, the at least one target precursor comprising a peptide and the plurality of constituent elements comprising amino acids.

Example 12 is the apparatus of Example 9, the NM-MD relationship information comprising a graph of nominal mass versus mass defect for the plurality of ion fragments.

Example 13 is the apparatus of Example 9, the at least one fragment lower boundary comprising a first regression line fit, a first upper boundary, and a first lower boundary a threshold distance from the first regression line fit.

Example 14 is the apparatus of Example 13, the first regression line fit comprising a line fit between a $Y_{max}$ ion and a $Y_1$ ion.

Example 15 is the apparatus of Example 14, the at least one fragment lower boundary comprising a second regression line fit, a second upper boundary, and a second lower boundary a threshold distance from the first regression line fit.

Example 16 is the apparatus of Example 15, the second regression line fit comprising a line fit between a $B_{max}$ ion and a $B_1$ ion.

Example 17 is a computer-readable storage medium, comprising a plurality of instructions that, when executed, enable processing circuitry to access at least one product ion data set generated via mass analyzing a sample comprising at least one target precursor, access precursor composition information for a plurality of constituent elements of the at least one target precursor, the precursor composition information comprising nominal mass information and mass defect information for at least a portion of the plurality of constituent elements, determine nominal mass (NM)-mass defect (MD) relationship information for a plurality of ion fragments associated with the at least one target precursor based on the precursor composition information, determine at least one ion fragment upper boundary and at least one ion fragment lower boundary for the plurality of ion fragments, extract a plurality of candidate ion fragments from the plurality of ion fragments via applying the at least one ion fragment upper boundary and the at least one ion fragment lower boundary to the NM-MD relationship information, and determine a plurality of target ion fragments from the plurality of candidate ion fragments based on fragmentation efficiency information associated with the plurality of candidate ion fragments.

Example 18 is the computer-readable storage medium of Example 17, the plurality of instructions, when executed, to enable the processing circuitry to generate spectral data for the plurality of target ion fragments.

Example 19 is the computer-readable storage medium of Example 17, the at least one target precursor comprising a peptide and the plurality of constituent elements comprising amino acids.

Example 20 is the computer-readable storage medium of Example 17, the NM-MD relationship information comprising a graph of nominal mass versus mass defect for the plurality of ion fragments.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

It is emphasized that the Abstract of the Disclosure is provided to comply with 315 C.F.R. § 1.152(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment. In the appended claims, the terms "including" and "in which" are used as the plain-English equivalents of the respective terms "comprising" and "wherein," respectively. Moreover, the terms "first," "second," and "third," etc. are used merely as labels, and are not intended to impose numerical requirements on their objects.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method of sample analysis, the method comprising:
accessing at least one product ion data set generated via mass analyzing a sample comprising at least one target precursor;
accessing precursor composition information for a plurality of constituent elements of the at least one target precursor, the precursor composition information comprising nominal mass information and mass defect information for at least a portion of the plurality of constituent elements;
determining nominal mass (NM)-mass defect (MD) relationship information comprising NM versus MD information for a plurality of ion fragments associated with the at least one target precursor, the NM-MD relationship information determined based on the precursor composition information;

determining at least one ion fragment upper boundary of the NM versus MD information for the plurality of ion fragments and at least one ion fragment lower boundary of the NM versus MD information for the plurality of ion fragments, wherein the plurality of ion fragments comprise Y-ions and complimentary B-ions, the at least one ion fragment lower boundary determined based on the plurality of Y-ions and the at least one ion fragment upper boundary determined based on the plurality of B-ions;

extracting a plurality of candidate ion fragments from the plurality of ion fragments via applying the at least one ion fragment upper boundary and the at least one ion fragment lower boundary to the NM versus MD information; and determining a plurality of target ion fragments from the plurality of candidate ion fragments based on fragmentation efficiency information associated with the plurality of candidate ion fragments.

2. The method of claim 1, the NM-MD relationship information comprising a graph of nominal mass versus mass defect for the plurality of ion fragments.

3. The method of claim 1, the at least one ion fragment lower boundary comprising the lower line fit, a first upper boundary, and a first lower boundary a threshold distance from the first regression line fit.

4. The method of claim 3, the at least one ion fragment upper boundary comprising the upper line fit, a second upper boundary, and a second lower boundary a threshold distance from the first regression line fit.

5. The computer-implemented method of claim 1, the plurality of candidate ion fragments comprising ion fragments arranged between the at least one ion fragment upper boundary and the at least one ion fragment lower boundary in the NM versus MD information.

6. The computer-implemented method of claim 1, the ion fragment upper boundary and the ion fragment lower boundary determined based on at least one standard deviation of NM and MD from at least one of the plurality of constituent elements.

7. The method of claim 1, the at least one ion fragment lower boundary comprising a lower line fit between a $Y_{max}$ ion and a $Y_1$ ion and the at least one ion fragment upper boundary comprising an upper line fit between a $B_{max}$ ion and a $B_1$ ion.

8. The method of claim 7, wherein the $Y_{max}$ ion and the $Y_1$ ion represent a highest and lowest mass-to-charge ratio product ion, respectively, and the $B_{max}$ ion and the $B_1$ ion represent a fragment ion having a highest B-ion mass-to-charge ratio and a lowest B-ion mass-to-charge ratio, respectively.

9. An apparatus operative to perform sample analysis, the apparatus comprising:

a processing circuitry; and logic, coupled to at least one memory, to:

access at least one product ion data set generated via mass analyzing a sample comprising at least one target precursor, access precursor composition information for a plurality of constituent elements of the at least one target precursor, the precursor composition information comprising nominal mass information and mass defect information for at least a portion of the plurality of constituent elements, determine nominal mass (NM)-mass defect (MD) relationship information for a plurality of ion fragments associated with the at least one target precursor, the NM-MD relationship determined based on the precursor composition information, determine at least one ion fragment upper boundary for the plurality of ion fragments and at least one ion fragment lower boundary for the plurality of ion fragments, wherein the plurality of ion fragments comprise Y-ions and complimentary B-ions, the at least one ion fragment lower boundary determined based on the plurality of Y-ions and the at least one ion fragment upper boundary determined based on the plurality of B-ions, extract a plurality of candidate ion fragments from the plurality of ion fragments via applying the at least one ion fragment upper boundary and the at least one ion fragment lower boundary to the NM-MD relationship information, and determine a plurality of target ion fragments from the plurality of candidate ion fragments based on fragmentation efficiency information associated with the plurality of candidate ion fragments.

10. The apparatus of claim 9, the NM-MD relationship information comprising a graph of nominal mass versus mass defect for the plurality of ion fragments.

11. The apparatus of claim 9, the at least one ion fragment lower boundary comprising comprising the lower line fit, a first upper boundary, and a first lower boundary a threshold distance from the first regression line fit.

12. The apparatus of claim 11, the at least one ion fragment upper boundary comprising the upper line fit, a second upper boundary, and a second lower boundary a threshold distance from the first regression line fit.

13. The apparatus of claim 9, the plurality of candidate ion fragments comprising ion fragments arranged between the at least one ion fragment upper boundary and the at least one ion fragment lower boundary in the NM versus MD information.

14. The apparatus of claim 9, the ion fragment upper boundary and the ion fragment lower boundary determined based on at least one standard deviation of NM and MD from at least one of the plurality of constituent elements.

15. The apparatus of claim 9, the at least one ion fragment lower boundary comprising a lower line fit between a $Y_{max}$ ion and a $Y_1$ ion and the at least one ion fragment upper boundary comprising an upper line fit between a $B_{max}$ ion and a $B_1$ ion.

16. The apparatus of claim 15, wherein the $Y_{max}$ ion and the $Y_1$ ion represent a highest and lowest mass-to-charge ratio product ion, respectively, and the $B_{max}$ ion and the $B_1$ ion represent a fragment ion having a highest B-ion mass-to-charge ratio and a lowest B-ion mass-to-charge ratio, respectively.

17. A computer-readable storage medium, comprising a plurality of instructions that, when executed, enable processing circuitry to:

access at least one product ion data set generated via mass analyzing a sample comprising at least one target precursor;

access precursor composition information for a plurality of constituent elements of the at least one target precursor, the precursor composition information comprising nominal mass information and mass defect information for at least a portion of the plurality of constituent elements;

determine nominal mass (NM)-mass defect (MD) relationship information comprising NM versus MD information for a plurality of ion fragments associated with the at least one target precursor, the NM-MD relationship information determined based on the precursor composition information;

determine at least one ion fragment upper boundary of the NM versus MD information for the plurality of ion fragments and at least one ion fragment lower boundary of the NM versus MD information for the plurality of ion fragments, wherein the plurality of ion fragments comprise Y-ions and complimentary B-ions, the at least one ion fragment lower boundary determined based on the plurality of Y-ions and the at least one ion fragment upper boundary determined based on the plurality of B-ions;

extract a plurality of candidate ion fragments from the plurality of ion fragments via applying the at least one ion fragment upper boundary and the at least one ion fragment lower boundary to the NM versus MD information; and determine a plurality of target ion fragments from the plurality of candidate ion fragments based on fragmentation efficiency information associated with the plurality of candidate ion fragments.

18. The computer-readable storage medium of claim 17, the NM-MD relationship information comprising a graph of nominal mass versus mass defect for the plurality of ion fragments.

19. The computer-readable storage medium of claim 17, the plurality of candidate ion fragments comprising ion fragments arranged between the at least one ion fragment upper boundary and the at least one ion fragment lower boundary in the NM versus MD information.

20. The computer-readable storage medium of claim 17, the ion fragment upper boundary and the ion fragment lower boundary determined based on at least one standard deviation of NM and MD from at least one of the plurality of constituent elements.

21. The medium of claim 17, the at least one ion fragment lower boundary comprising a lower line fit between a $Y_{max}$ ion and a $Y_1$ ion and the at least one ion fragment upper boundary comprising an upper line fit between a $B_{max}$ ion and a $B_1$ ion.

22. The medium of claim 21, wherein the $Y_{max}$ ion and the $Y_1$ ion represent a highest and lowest mass-to-charge ratio product ion, respectively, and the $B_{max}$ ion and the $B_1$ ion represent a fragment ion having a highest B-ion mass-to-charge ratio and a lowest B-ion mass-to-charge ratio, respectively.

* * * * *